US011763947B2

(12) United States Patent
Baronov et al.

(10) Patent No.: US 11,763,947 B2
(45) Date of Patent: Sep. 19, 2023

(54) SYSTEM AND METHOD FOR PROVIDING CLINICAL DECISION SUPPORT

(71) Applicant: Etiometry, Inc., Boston, MA (US)

(72) Inventors: Dimitar V. Baronov, Weston, MA (US); Robert Hammond-Oakley, Somerville, MA (US); Evan J. Butler, New Haven, CT (US)

(73) Assignee: Etiometry Inc., Boston, MA (US)

( * ) Notice: Subject to any disclaimer, the term of this patent is extended or adjusted under 35 U.S.C. 154(b) by 71 days.

(21) Appl. No.: 17/402,256

(22) Filed: Aug. 13, 2021

(65) Prior Publication Data
US 2022/0115129 A1  Apr. 14, 2022

Related U.S. Application Data

(60) Provisional application No. 63/091,493, filed on Oct. 14, 2020, provisional application No. 63/091,427, (Continued)

(51) Int. Cl.
*G16H 50/20* (2018.01)
*G16H 20/00* (2018.01)
(Continued)

(52) U.S. Cl.
CPC ............. *G16H 50/20* (2018.01); *G16H 10/60* (2018.01); *G16H 20/00* (2018.01); *G16H 50/70* (2018.01)

(58) Field of Classification Search
CPC ........ G16H 50/20; G16H 50/70; G16H 10/60; G16H 20/00
(Continued)

(56) References Cited

U.S. PATENT DOCUMENTS 6,273,088 B1  8/2001 Hillsman
6,322,502 B1  11/2001 Schoenberg et al.
(Continued)

FOREIGN PATENT DOCUMENTS

DE    202013012876 U1    4/2021
EP        3767636 A1      1/2021
(Continued)

OTHER PUBLICATIONS

International Searching Authority, International Search Report—International Application No. PCT/US2021/055094, dated Feb. 8, 2022 together with the Written Opinion of the International Searching Authority, 265 pages.
(Continued)

*Primary Examiner* — Carl H Layno
*Assistant Examiner* — Michael J Lau
(74) *Attorney, Agent, or Firm* — Nutter McClennen & Fish LLP

(57) ABSTRACT

A system determines patient eligibility for a medical protocol. The system includes a medical protocol library containing information relating to a plurality of medical protocols. The information includes eligibility rules and compliance rules for the plurality of medical protocols. The system also includes a sensor and medical device interface configured to receive patient data from one or more sensors and/or one or more medical device. The patient data relates to the eligibility rules and/or the compliance rules for at least one of the medical protocols. The system also includes a protocol eligibility module configured to determine patient eligibility for at least one of the medical protocols as a function of the received patient data. Furthermore, the system includes a user interface configured to display an indication that the patient is eligible for the protocol.

20 Claims, 19 Drawing Sheets

Related U.S. Application Data filed on Oct. 14, 2020, provisional application No. 63/180,881, filed on Apr. 28, 2021, provisional application No. 63/183,979, filed on May 4, 2021, provisional application No. 63/190,070, filed on May 18, 2021.

(51) Int. Cl.
  *G16H 50/70* (2018.01)
  *G16H 10/60* (2018.01)
(58) Field of Classification Search
  USPC ........................................................ 600/300
  See application file for complete search history.

(56) References Cited

U.S. PATENT DOCUMENTS

| | | | |
|---|---|---|---|
| 6,463,930 B2 | 10/2002 | Biondi et al. | |
| 6,662,032 B1 | 12/2003 | Gavish et al. | |
| 6,668,829 B2 | 12/2003 | Biondi et al. | |
| 7,017,574 B2 | 3/2006 | Biondi et al. | |
| 7,334,578 B2 | 2/2008 | Biondi et al. | |
| 7,454,359 B2 | 11/2008 | Rosenfeld et al. | |
| 7,530,353 B2 | 5/2009 | Choncholas et al. | |
| 7,850,619 B2 | 12/2010 | Gavish et al. | |
| 8,021,309 B2 | 9/2011 | Zilberg | |
| 8,307,827 B2 | 11/2012 | Martin et al. | |
| 8,333,708 B2 | 12/2012 | Rapoport et al. | |
| 8,340,749 B2 | 12/2012 | Sugimachi et al. | |
| 8,418,692 B2 | 4/2013 | Sanchez | |
| 8,561,612 B2 | 10/2013 | Heinonen | |
| 8,677,996 B2 | 3/2014 | Sanchez | |
| 8,695,593 B2 | 4/2014 | Tehrani | |
| 8,789,529 B2 | 7/2014 | Vandine et al. | |
| 8,998,830 B2 | 4/2015 | Halperin et al. | |
| 9,327,090 B2 | 5/2016 | Steinhauer et al. | |
| 9,533,113 B2 | 1/2017 | Lain et al. | |
| 9,757,041 B2 | 9/2017 | Grudic et al. | |
| 9,776,005 B2 | 10/2017 | Meyyappan et al. | |
| 10,149,647 B2 | 12/2018 | Wu et al. | |
| 10,179,217 B2 | 1/2019 | Steinhauer et al. | |
| 10,245,399 B2 | 4/2019 | Martin et al. | |
| 10,271,739 B2 | 4/2019 | Freeman et al. | |
| 10,331,853 B2 | 6/2019 | Rosenblatt et al. | |
| 10,490,309 B1 | 11/2019 | McNair | |
| 10,653,368 B1 | 5/2020 | McNair | |
| 10,702,166 B1 | 7/2020 | Freeman et al. | |
| 10,765,822 B2 | 9/2020 | Dong et al. | |
| 10,765,823 B2 | 9/2020 | Laksov | |
| 2005/0205093 A1 | 9/2005 | Jabour | |
| 2006/0155206 A1* | 7/2006 | Lynn | A61B 5/4818 600/323 |
| 2007/0191697 A1* | 8/2007 | Lynn | A61B 5/082 600/323 |
| 2007/0239043 A1* | 10/2007 | Patel | G16H 50/20 600/515 |
| 2008/0236582 A1 | 10/2008 | Tehrani | |
| 2009/0137919 A1 | 5/2009 | Bar-Lavie et al. | |
| 2010/0000526 A1 | 1/2010 | Rittner | |
| 2010/0057490 A1 | 3/2010 | Kocis et al. | |
| 2010/0218766 A1 | 9/2010 | Milne | |
| 2011/0108034 A1 | 5/2011 | Viertio-Oja | |
| 2012/0192867 A1 | 8/2012 | Lewis et al. | |
| 2013/0054264 A1 | 2/2013 | Baronov et al. | |
| 2013/0085775 A1 | 4/2013 | Baronov et al. | |
| 2013/0173303 A1 | 7/2013 | Hyde et al. | |
| 2013/0185097 A1* | 7/2013 | Saria | G06Q 10/00 705/3 |
| 2013/0231949 A1 | 9/2013 | Baronov et al. | |
| 2013/0267791 A1* | 10/2013 | Halperin | A61B 5/742 600/300 |
| 2014/0136225 A1 | 5/2014 | Badawi | |
| 2014/0142970 A1 | 5/2014 | Baronov et al. | |
| 2014/0235959 A1 | 8/2014 | Jafari et al. | |
| 2014/0249845 A1 | 9/2014 | Kahn et al. | |
| 2014/0371618 A1* | 12/2014 | Steinhauer | A61M 16/0051 600/300 |
| 2015/0059756 A1 | 3/2015 | Baronov et al. | |
| 2015/0157275 A1* | 6/2015 | Swamy | A61B 5/0816 600/301 |
| 2015/0208968 A1 | 7/2015 | Ennett et al. | |
| 2015/0213221 A1* | 7/2015 | Bravi | G16H 50/30 702/19 |
| 2015/0347704 A1* | 12/2015 | Baronov | G16H 50/30 600/301 |
| 2016/0193437 A1 | 7/2016 | Bao | |
| 2017/0028146 A1 | 2/2017 | Nandigama | |
| 2017/0071549 A1* | 3/2017 | Seely | A61B 5/7203 |
| 2017/0164909 A1 | 6/2017 | Freeman et al. | |
| 2017/0232214 A1 | 8/2017 | Walsh | |
| 2018/0001042 A1 | 1/2018 | Albanese et al. | |
| 2018/0169335 A1 | 6/2018 | Baronov et al. | |
| 2018/0280645 A1 | 10/2018 | Lellouche et al. | |
| 2018/0280646 A1 | 10/2018 | Freeman et al. | |
| 2018/0325463 A1 | 11/2018 | Walsh | |
| 2018/0366253 A1 | 12/2018 | Baronov et al. | |
| 2019/0091403 A1* | 3/2019 | Osorio | G16H 40/63 |
| 2019/0224434 A1* | 7/2019 | Silver | A61H 31/00 |
| 2019/0287661 A1 | 9/2019 | Nobre et al. | |
| 2019/0321574 A1 | 10/2019 | Sallee et al. | |
| 2020/0168334 A1* | 5/2020 | Mowery | G06N 3/08 |
| 2020/0179206 A1 | 6/2020 | Gadgil et al. | |
| 2020/0337648 A1* | 10/2020 | Saripalli | G16H 50/30 |
| 2021/0090742 A1 | 3/2021 | Baronov et al. | |
| 2021/0104328 A1 | 4/2021 | Baronov et al. | |
| 2021/0228794 A1* | 7/2021 | Lecamwasam | A61M 1/3643 |
| 2022/0115129 A1 | 4/2022 | Baronov et al. | |
| 2022/0115131 A1 | 4/2022 | Baronov et al. | |
| 2022/0115132 A1 | 4/2022 | Baronov et al. | |
| 2022/0115143 A1 | 4/2022 | Baronov et al. | |

FOREIGN PATENT DOCUMENTS

| | | |
|---|---|---|
| IL | 234722 A | 2/2019 |
| IL | 264507 A | 9/2020 |
| IL | 277521 A | 1/2022 |
| JP | 6262200 B2 | 1/2018 |
| JP | 6524196 B2 | 6/2019 |
| TW | 200720955 A | 6/2007 |
| WO | 2012/122096 A2 | 9/2012 |
| WO | 2013/142268 A1 | 9/2013 |
| WO | 2014/078859 A1 | 5/2014 |
| WO | 2021/062292 A1 | 4/2021 |
| WO | 2022/081918 A1 | 4/2022 |
| WO | 2022/081926 A1 | 4/2022 |

OTHER PUBLICATIONS

[No Author Listed] Every breath you take: Managing ventilation in the ICU with data, Published Jun. 20, 2019. Retreived from the internet under https://www.gehealthcare.com/article/every-breath-you-take-managing-ventilation-in-the-icu-with-data on Jun. 9, 2020. 5 pages.

Brochard, L., et al., "Comparison of three methods of gradual withdrawal from ventilatory support during weaning from mechanical ventilation," American Journal of Respiratory Critical Care Medicine, 2009 vol. 150, Issue 4, pp. 1-6.

Dojat, M., et al., "Evaluation of a knowledge-based system providing ventilatory management and decision for extubation," submitted on Jul. 7, 2009, 35 pages.

Esteban, A., et al., "Evolution of Mechanical Ventilation in Response to Clinical Research," American Journal of Respiratory Critical Care Medicine, 2009 vol. 177, pp. 170-177.

Macnaughton, P., "Weaning ventilatory support," 2004 The Medicine Publishing Company Ltd, 2004, pp. 392-393.

Randolph, A., et al., "Effect of Mechanical Ventilator Weaning Protocols on Respiratory Outcomes in Infants and Children," Caring for the Critically Ill Patient, (reprinted), Nov. 27, 2002, vol. 288, No. 20, pp. 2561-2568.

(56) References Cited

OTHER PUBLICATIONS

Yang, K., et al., "A prospective Study of Indexes Predicting the Outcome of Trials of Weaning from Mechanical Ventilation," vol. 324, No. 21, May 23, 1991. pp. 1445-1450.
International Searching Authority, International Search Report—International Application No. PCT/US21/55103, dated Jan. 24, 2021 together with the Written Opinion of the International Searching Authority, 22 pages.

* cited by examiner

Extubation Readiness Test Protocol

Inclusion Criteria

Patient on PICU or CICU service

Patient spontaneously breathing

PEEP ≤ 7.0 cmH2O

FiO2 ≤ 0.5

Compliance

SpO2 ≥ goal SpO2

Exhaled TV ≥ 5mL/kg ideal body weight

RR not increased by 20% above baseline RR

HR not increased by 20% above baseline HR

*FIG. 4*

Clinical Protocol   120
- Eligibility rules  122
  - Eligibility VAR 1 > x
  - Eligibility VAR 2 < y
  - Eligibility COND 1 is True
- Compliance rules  124
  - Compliance VAR 1 > x
  - Compliance VAR 2 < y
- Protocol trigger  126
  - IF X True Start Protocol
- Subscription rules  128
  - Sub Level 1
    - Direct care team – Nurse, RT, Fellow(s)
  - Sub Level 2
    - Management team – Attending, Nurse Manager, RT Manager
  - Sub Level N
- Notification Rules  130
  - Sub Level 1
    - Eligibility status change – Notification 1
    - Protocol enrollment – Notification 2
    - Out of compliance – Notification 3
  - Sub Level 2
    - Eligibility status change – No notification
    - Protocol enrollment – Notification 1
    - Out of compliance – Notification 1
  - ...

*FIG. 6*

Extubating Readiness Trial (ERT) Protocol 120

- Eligibility rules 122
    - FiO2 <= 0.5
    - PEEP < 7 cm $H_2O$
    - Patient is mechanically ventilated
- Compliance rules 124
    - SpO2 > 88%
    - Tidal Volume > 5 ml/kg
    - (EtCO2 – EtCO2 @ baseline)/EtCO2 @ baseline < 1.2
    - (HR – HR @ baseline) / HR @ baseline < 1.2
    - Patient is on Pressure Support ventilation
- Trigger 126
    - Vent mode is Pressure Support

120A — Ventilation Protocol (Vent)
- Eligibility rules 122
  - No data from ventilator
  - Risk for inadequate ventilation of $CO_2 > 20\%$ or: 125
  - $SpO_2 < 92\%$ with $FiO_2 > 80\%$
- Compliance rules 124
  - $SpO_2 > 88$
  - $SpO_2 < 96$
  - $TV < 8\ ml/Kg$
  - Risk for inadequate 125 ventilation of $CO_2 < 20\%$
  - Increase PEEP by 1 cm $H_2O$ for every 30 min $FiO_2 > 60\%$
- Protocol trigger 126
  - Ventilator data starts streaming
  - Stop when extubated

120B — Ventilation Weaning Protocol (Vent W)
- Eligibility rules: 122
  - ≥90% dynamic concordance for Ventilation protocol for more than 3 h
- Compliance rules 124
  - $SpO_2 > 88$
  - $SpO_2 < 96$
  - $TV < 8\ ml/Kg$
  - Risk for inadequate ventilation of $CO_2 < 20\%$ 125
  - PEEP drops by 2 cm $H_2O$ for every hour of patient compliance with ventilation until:
    - $FiO_2 < 0.5$
    - PEEP < 7 cm $H_2O$
- Protocol trigger 126
  - Start automatically after patient eligible for more than 6 hours
  - Stop Automatically when patient compliant and:
    - $FiO_2 < 0.5$
    - PEEP < 7 cm $H_2O$

120C — Extubation Readiness Protocol (ERT)
- Eligibility rules 122
  - $FiO_2 <= 0.5$
  - PEEP < 7 cm $H_2O$
  - Patient is mechanically ventilated
- Compliance rules 124
  - $SpO_2 > 88\%$
  - Tidal Volume > 5 ml/kg
  - $(EtCO_2 - EtCO_2\ @\ baseline)/EtCO_2\ @\ baseline < 1.2$
  - $(HR - HR\ @\ baseline)/HR\ @\ baseline < 1.2$
  - Patient is on Pressure Support ventilation
  - Risk for inadequate ventilation of $CO_2 < 20\%$ 125
  - Risk for inadequate oxygen delivery < 10% 125
- Trigger 126
  - Start when vent mode is Pressure Support
  - Stop when mode is switched

SYSTEM AND METHOD FOR PROVIDING CLINICAL DECISION SUPPORT

CROSS-REFERENCE TO RELATED APPLICATIONS

This application claims the benefit of U.S. Provisional Patent Application No. 63/091,493, filed Oct. 14 2020, U.S. Provisional Patent Application No. 63/091,427, filed Oct. 14, 2020, U.S. Provisional Patent Application No. 63/180,881, filed Apr. 28, 2021, U.S. Provisional Patent Application No. 63/183,979, filed May 4, 2021, and U.S. Provisional Patent Application No. 63/190,070, filed May 18, 2021, each of which is incorporated by reference herein in its entirety.

STATEMENT REGARDING FEDERALLY SPONSORED RESEARCH OR DEVELOPMENT

This invention was made with government support under R44HL117340 awarded by the National Heart, Lung, and Blood Institute of the National Institutes of Health. The government has certain rights in the invention.

FIELD OF THE INVENTION

Illustrative embodiments of the invention generally relate to systems and methods for patient monitoring and, more particularly, illustrative embodiments relate to determining whether a patient qualifies for a medical protocol.

BACKGROUND OF THE INVENTION

Practicing medicine is becoming increasingly more complicated due to the introduction of new sensors and treatments. As a result, clinicians are confronted with an avalanche of patient data, which needs to be evaluated and well understood in order to prescribe the optimal treatment from the multitude of available options, while reducing patient risks. One environment where this avalanche of information has become increasingly problematic is the Intensive Care Unit (ICU). There, the experience of the attending physician and the physician's ability to assimilate the available physiologic information have a significant impact on the clinical outcome. Hospitals that do not maintain trained intensivists around the clock experience a 14.4% mortality rate as opposed to a 6.0% rate for fully staffed centers. It is estimated that raising the level of care to that of average trained physicians across all ICUs can save 160,000 lives and $4.3 Bn annually. As of 2012, there is a shortage of intensivists, and projections estimate the shortage will only worsen, reaching a level of 35% by 2020.

The value of experience in critical care can be explained by the fact that clinical data in the ICU is delivered at a rate far greater than even the most talented physician can absorb, and studies have shown that errors are six times more likely under conditions of information overload and eleven time more likely with an acute time shortage. Moreover, treatment decisions in the ICU heavily rely on clinical signs that are not directly measurable, but are inferred from other physiologic information. Thus, clinician expertise and background play a more significant role in the minute to minute decision making process.

SUMMARY OF VARIOUS EMBODIMENTS

In accordance with one embodiment of the invention, a system determines patient eligibility and compliance with a medical protocol. The system includes a medical protocol library containing information relating to a plurality of medical protocol. The information includes eligibility rules and compliance rules for the plurality of medical protocols. The plurality of medical protocols may include at least one parent protocol and at least one child protocol. The system further includes a sensor and medical device interface configured to receive patient data from one or more sensors and/or one or more medical devices. The interface also receives the patient data relating to the eligibility rules and/or the compliance rules for at least one of the medical protocols. A protocol eligibility module is configured to determine patient eligibility for the at least one parent protocol as a function of the received patient data.

A user interface may be configured to display an indication that at least one patient is eligible for the at least one parent protocol. The system may include a protocol compliance module configured to determine, after the at least one patient enters the parent protocol, a dynamic concordance rate of the at least one patient for the parent protocol as a function of the received patient data and the compliance rules. The dynamic concordance rate defines the rate at which the patient data is consistent with the compliance rules of the parent protocol. The protocol eligibility module may be further configured to determine patient eligibility for the at least one child protocol as a function of the dynamic concordance rate of the at least one parent protocol. The user interface may also be further configured to display the dynamic concordance rate of the parent protocol for the at least one patient.

In various embodiments, the user interface is configured to display, in response to a user selection of a selected patient, all of the received patient data relating to the eligibility rules and/or the compliance rules of a corresponding protocol that the selected patient is on. In the user interface, non-compliant portions of the received data are visually distinguishable from compliant portions of the data.

The system may work with a plurality of protocols. For example, the medical protocol may be an extubation readiness trial. Patient eligibility for the protocol may be determined as a function of meeting a plurality of conditions and/or patient variables. To that end, the protocol eligibility module may be configured to determine patient eligibility as a function of a hidden state variable. The eligibility rules for the child protocol may include a threshold dynamic concordance rate of the parent protocol. Among other things, the protocol eligibility module may be configured to determine patient eligibility as a function of a patient electronic medical record.

The system may also include a quality reporting module configured to determine a protocol eligibility time. The protocol eligibility time is the amount of time elapsed from when the at least one patient is eligible for the medical protocol to the time the at least one patient is entered into the medical protocol. In some embodiments, the user interface is further configured to display the eligibility time for the at least one patient.

In accordance with yet another embodiment, a method enters a patient into a medical protocol. The method receives eligibility rules and compliance rules for a plurality of medical protocols. The plurality of medical protocols include a parent protocol and a child protocol. The method receives real-time patient data from one or more sensors and/or medical devices. The patient data directly or indirectly relates to the eligibility rules and/or the compliance rules for the parent protocol and/or the child protocol. The method determines that the patient is eligible for the parent protocol as a function of the eligibility rules and the real-time patient data from the one or more sensor and/or medical devices. An indication that the patient is eligible for the parent protocol is provided. A dynamic concordance rate for the parent protocol is calculated. The method determines that the patient is eligible for the child protocol as a function of the dynamic concordance rate of the parent protocol.

The method may also enter the patient into the medical protocol after indicating that the patient is eligible for the protocol. Additionally, or alternatively, the method may display an indication that the patient is eligible for the protocol. In various embodiments, determining patient eligibility is a function of a patient electronic medical record. After determining that the patient is eligible, the method may automatically transition the eligible patient into the protocol.

Among other things, the method may display, on a user interface, a plurality of patients that are eligible for the protocol and/or currently enrolled in the protocol. The method may also track a time since the patient became eligible for the protocol and/or a time since the patient has been enrolled in the protocol. The method may also track a dynamic concordance rate of the medical protocol. The time since the patient became eligible for the protocol, the time since the patient is enrolled in the protocol, and/or the dynamic concordance rate of the medical protocol may be displayed on the user interface.

The method may display, in response to a user selection of a given protocol, the received patient data that relates to the eligibility rules and/or the compliance rules for the selected protocol. The received patient data may be used to determine a hidden state variable. Among other things, the eligibility rules and/or the compliance rules for the selected protocol may include a hidden state variable risk.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 4 schematically shows eligibility rules and compliance rules for an example of an extubation readiness test protocol in accordance with illustrative embodiments.

FIG. 6 schematically shows a generic example of an executable medical protocol configuration having a variety of eligibility rules, compliance rules, and a protocol trigger in accordance with illustrative embodiments.

FIG. 7 schematically shows an example of a medical protocol for an extubation readiness trial having a variety of eligibility rules, compliance rules, and a protocol trigger in accordance with illustrative embodiments

FIG. 12 schematically shows an example of nested medical protocols having a variety of eligibility rules, compliance rules, and a protocol trigger in accordance with illustrative embodiments.

FIGS. 13A-13G schematically show an interface for viewing patient protocol information in accordance with illustrative embodiments.

DESCRIPTION OF ILLUSTRATIVE EMBODIMENTS

In illustrative embodiments, a system enables real-time tracking of patient eligibility for one or more protocols based on a variety of data relating to the patient. To that end, the system has access to data relating to a variety of medical protocols and parameters/rules for patient eligibility within the protocols. Each protocol is associated with a medical procedure, medical treatment, or medical intervention (generally referred to as a course of action). The system automatically streams and collects patient data to determine the real-time eligibility of the patient for the protocol. Prior to initiating a medical course of action (also referred to as initiating or beginning the protocol), the duration of eligibility compliance for different variables is tracked in a dynamic manner. After the patient begins a given protocol, the system tracks protocol compliance for different variables in a dynamic manner.

Illustrative embodiments further enable advanced protocols. For example, some protocols may use risk analytics (e.g., hidden internal state variables) to determine patient eligibility and/or compliance. Furthermore, illustrative embodiments additionally, or alternatively, enable nested protocols, where compliance with a first protocol (or more) is an eligibility criterion for a second protocol. Thus, the inventors discovered that new protocols could be created that use the dynamic concordance rate of another protocol as an eligibility and/or compliance rule.

Illustrative embodiments also provide an interactive display for medical practitioners that provides visualization for patient performance on the protocol. A display provides a listing of all patients under care of the medical practitioner or all patients in a particular unit, and further provides protocol status details for each patient. For example, illustrative embodiments provide visual indications of whether the patient is eligible for a course of action associated with the protocol and the amount of time the patient has been eligible. If the patient is on a protocol, illustrative embodiments provide visual indications of how long the patient has been on the protocol and how compliant the patient has been with the protocol. Some embodiments may provide a visual indication of the compliance rate per individual parameter of the protocol for each patient. After selecting the visual indication, a display shows the patient performance variables that are relative to the particular protocol. Details of illustrative embodiments are discussed below.

Figure 1:
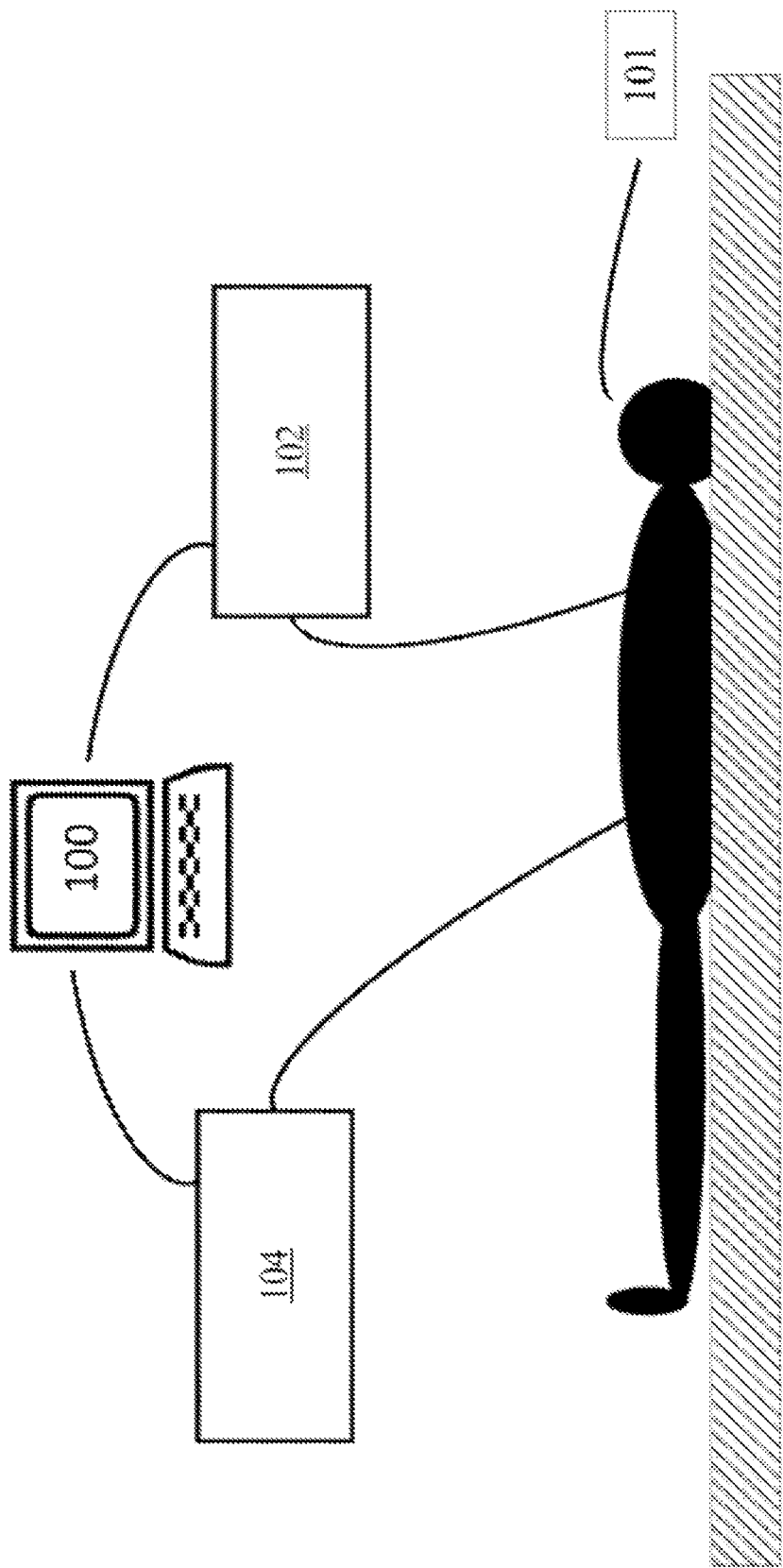
FIG. 1 schematically shows a clinical patient environment in accordance with illustrative embodiments of the invention.

FIG. 1 schematically shows a clinical patient environment in accordance with illustrative embodiments of the invention. The environment includes sensors 102 (also referred to as monitors 102) for providing patient data to health providers, such as physicians, nurses, or other medical care providers. To that end, a patient 101 may be coupled to one or more physiological sensors 102 or bedside monitors 102 that may monitor various physiological parameters of the patient. It should be noted that a patient 101 may be a human, or not human (a non-human being, e.g., a dog).

The sensors 102 may include, but are not limited to, a blood oximeter, a blood pressure measurement device, a pulse measurement device, a glucose measuring device, one or more analyte measuring devices, an electrocardiogram recording device, amongst others. In addition, the patient 101 may be administered routine exams and tests and the data may be stored in an electronic medical record (EMR) 103 (shown in FIG. 2). The electronic medical record 103 may include but is not limited to stored information such as hemoglobin, arterial and venous oxygen content, lactic acid, weight, age, sex, ICD-10 code, capillary refill time, subjective clinician observations, patient self-evaluations, prescribed medications, medications regiments, genetics, test results, allergies, etc.

In addition, the patient 101 may be coupled to one or more treatment devices 104 that are configured to administer treatments to the patient. In some embodiments, one or more treatment devices 104 may be controlled by a system 100 as disclosed herein, for example in response to output defining a patient state or medical condition from a trajectory interpreter module. In various embodiments, the treatment devices 104 may include extracorporeal membrane oxygenator, mechanical ventilator, medication infusion pumps, implantable ventricular assist devices, etc.

Illustrative embodiments provide real-time automatic determination of whether the patient 101 is eligible for a course of action of the medical protocol (referred to generally as being eligible for the protocol) based at least partially on data acquired directly from the sensors and peripheral devices. The real-time determination is advantageous over prior art methods that require the medical practitioner to review disparate patient data reports and analyze the data to determine whether the patient 101 is eligible for the protocol. Additionally, the medical practitioner generally checks patient eligibility sporadically, leading to sub-optimal clinical outcomes in cases where optimal medical treatment for the patient 101 requires early initiation of the protocol. In a similar manner, sporadic eligibility checks fail to account for the dynamic concordance of the patient's eligibility because the measurements are taken at a static moment in time.

The system 100 may track how long a patient variable has been in compliance with a set eligibility criteria, advantageously improving medical protocol technology by enabling new protocols that have a longitudinal (e.g., sustained time basis) criteria, as opposed to protocols that use the most-recent static data points. Accordingly, illustrative embodiments track dynamic concordance, or the rate at which patient physiological data is consistent with the requirements of a protocol after the protocol is initiated. This advantageously allows medical practitioners to visualize the patient data as a percentage compliance per time duration (e.g., 60% dynamic concordance in the 3 hours since protocol began). Furthermore, tracking eligibility time advantageously allows medical practitioners to prioritize patients who have been eligible for a long time, thus mitigating any risk emanating from the fact that they have not been getting the prescribed protocol treatment for prolonged duration.

The dynamic concordance calculation based on longitudinal measurements of patient variables also supports using the metric as an actionable therapeutic target and consequently administering treatment targeted at increasing the concordance rate of the patient. Furthermore, the inventors have preliminary data indicating that patients achieving a desired dynamic concordance rate may experience better outcomes relative to patients that have lower concordance rate.

By providing continuous real-time assessment of whether the patient trajectory is progressing according to a protocol specified pathway, the dynamic concordance affords more focused and timely intervention to keep the patient within the most advantageous course, which is a significant improvement relative to what is possible with current technology. The longer time the patient spends within the desired trajectory as measured by the concordance rate the higher is the likelihood that the patient will not experience complications and achieve the optimal possible clinical outcome. Conversely, the less time the patient spends within the desired trajectory as measured by the concordance rate the higher the likelihood that the patient will experience complications and not achieve the optimal clinical outcome.

To that end, a patient protocol eligibility and compliance system, generally referred to herein as system 100, may be configured to receive patient related information, including real-time information from the sensors 102, EMR patient information from the electronic medical record 103, information from the treatment devices 104, such as ventilatory settings, infusion rates, types of medications, and other patient related information, which may include the patient's medical history, previous treatment plans, results from previous and present lab work, allergy information, predispositions to various conditions, and any other information that may be deemed relevant to make.

The system 100 provides real-time protocol eligibility updates. Additionally, illustrative embodiments may determine the extent of time that the patient 101 is eligible for a protocol. Accordingly, medical practitioners may have quantifiable standards by which medical practitioner performance is judged (e.g., time from eligibility to protocol initiation, protocol compliance rate, etc.).

Figure 2:
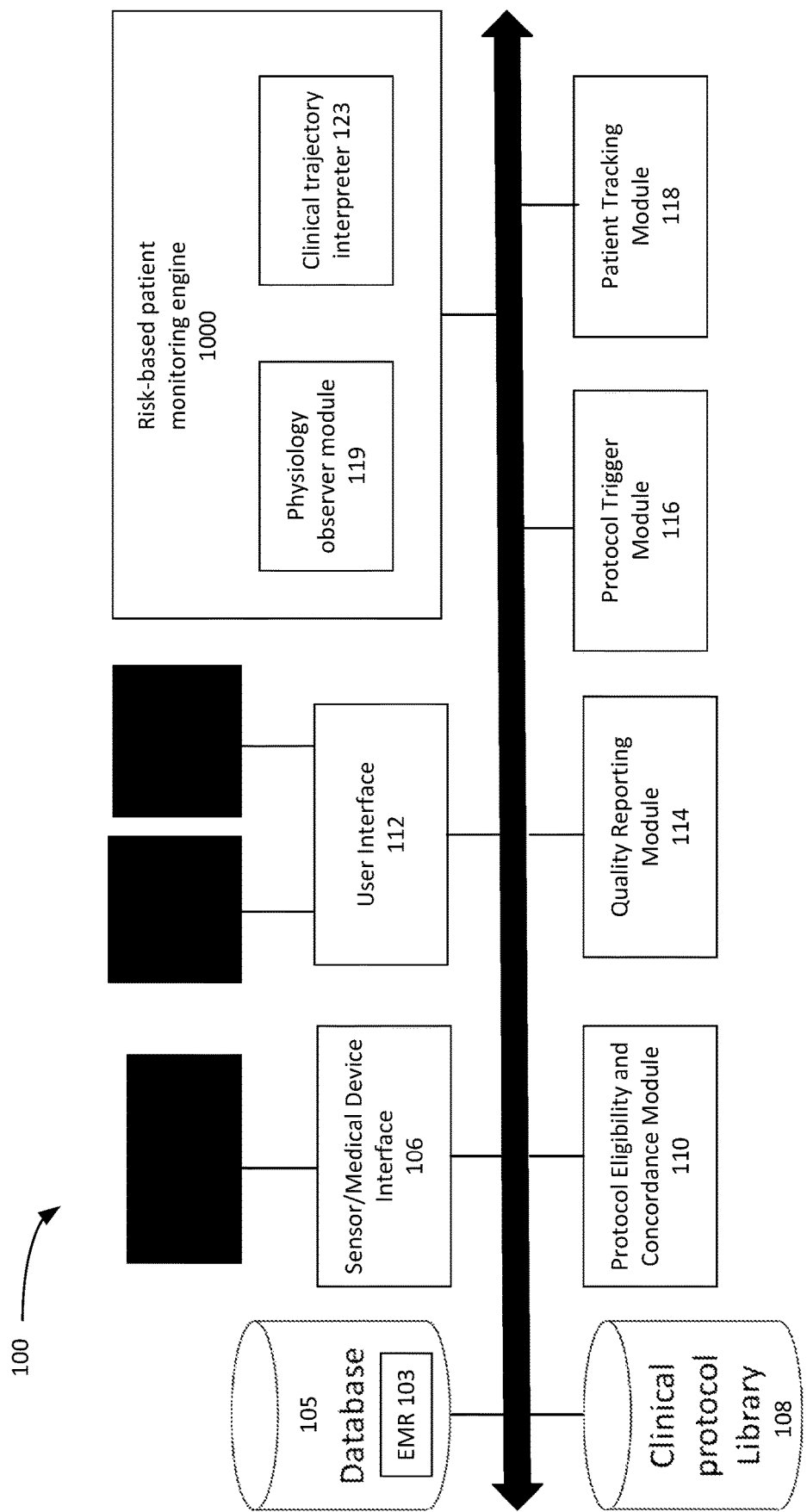
FIG. 2 schematically shows details of a system in accordance with illustrative embodiments of the invention.

FIG. 2 schematically shows details of the system 100 in accordance with illustrative embodiments of the invention. The system 100 includes a sensor/medical device interface 106 configured to communicate with the one or more sensors 102 and/or one or more medical devices 104. For convenience, illustrative embodiments may refer to receiving data from one or more sensors and/or one or more medical devices generally as receiving data from the sensors 102. However, it should be understood that discussion of receiving data from the sensors 102 is intended to also include receiving data from the medical devices 104.

To reiterate, the interface 106 receives/ streams real-time patient data from the sensors 102. The interface 106 may receive data from a variety of sensors 102, such as blood oximeter, a blood pressure measurement device, a pulse measurement device, a glucose measuring device, one or more analyte measuring devices, an electrocardiogram recording device, amongst others. In some embodiments, the interface 106 simultaneously communicates with a plurality of sensors 102 and/or medical devices. Accordingly, the interface 106 may aggregate and/or compile the various received patient data.

The system 100 includes a database 105 having access to the patient EMR 103, as described previously. The database 105 may also communicate with the sensor interface 106 to store the real-time data as it is received via the interface 106. The system 100 also includes a medical protocol library 108 containing information relating to a plurality of medical protocols. As an example, the medical protocol may include an extubation readiness trial protocol, ventilation vasoactive weaning protocol, sepsis management protocol, enhanced recovery after surgery (ERAS) protocols, and/or other hospital protocols. The information in the library 108 includes eligibility rules and compliance rules for each of the protocols, which are discussed in more detail further below. The library 108 may also include specific subscription rules and/or notification rules for each protocol, which are discussed in more detail further below.

A protocol eligibility and compliance module 110 is configured to determine patient eligibility for at least one of the medical protocols as a function of the received patient data. Additionally, the eligibility and compliance module 110 may access historic data and/or the EMR 103 from the database 105 to determine patient eligibility. To that end, the eligibility and compliance module 110 may communicate with, among other things, the interface 106, the database 105, and the library 108.

Generally, patient eligibility depends on one or more measurements of patient data meeting a threshold status according to the requirements of the protocol stored in the library 108 (e.g., a certain FiO2 and/or BPM measurement). When the patient 101 is eligible for a protocol, the eligibility module 110 triggers an indication that the patient 101 is eligible. In some embodiments, the eligibility module 110 sounds an alert and/or communicates with a user interface 112 to visually indicate the patient is eligible. In some embodiments, the user interface also communicates the amount of time the patient has been eligible. Thus, illustrative embodiments advantageously provide real-time updates as to patient eligibility status. The real-time data collection and eligibility updates contrast to prior art methods that rely on medical practitioners checking, collecting, aggregating, and analyzing a plurality of static patient parameters to determine protocol eligibility.

The determination of eligibility is based on a collection of measurement thresholds, events, and/or other binary variables. For example, eligibility rules for a vasoactive weaning protocol may include that the patients are under cardiac service (determined by the hospital ADT stream or EMR), are on medication drip (another event), have IDO2 index less than a threshold value, and have blood pressure greater than another threshold value.

Figure 3:
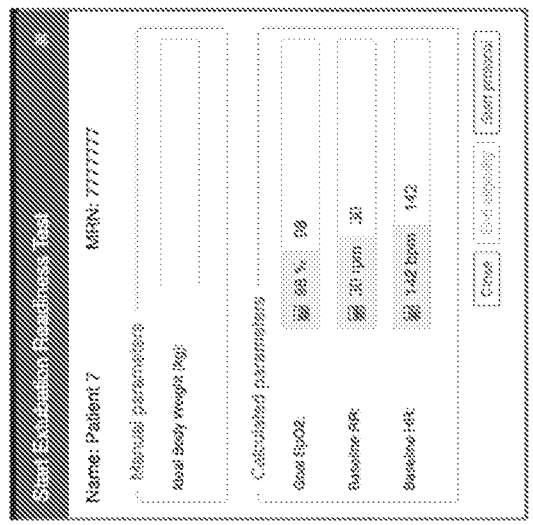
FIG. 3 schematically shows a notification through which a user may acknowledge patient eligibility and customize compliance rules in accordance with illustrative embodiments of the invention.

The system 100 may include a quality reporting module 114 that tracks the time elapsed from patient eligibility until a user acknowledges patient eligibility. FIG. 3 schematically shows a popup notification through which the user may acknowledge patient eligibility (e.g., on a touch screen display via user interface 112) in accordance with illustrative embodiments of the invention. Alternatively, or additionally, the quality reporting module 114 may track the time elapsed from patient eligibility until a medical practitioner begins the course of action associated with the eligible protocol for the patient 101. By tracking this information, medical practitioner performance may be objectively measured (e.g., which practitioners are the fastest responders and what are the impacts of fast response time on clinical outcomes).

The system 100 may also include a protocol trigger module 116 that instructs the eligibility and compliance module 110 to begin tracking patient 101 compliance data. The protocol trigger module 116 is configured to receive information regarding the initiation of a course of action in the protocol 120. In various embodiments, the medical practitioner may initiate the course of action based on the feedback from the eligibility module 110 and inform the protocol trigger module 116 (e.g., through the user interface) of the course of action initiation. In some embodiments, the protocol trigger module 116 is configured to automatically initiate the course of action by communicating with a treatment device 104 (e.g., after a medical practitioner approves the initiation via the user interface). In other embodiments, the protocol trigger module 116 can automatically detect that the practitioner has initiated the course of action and initiate tracking concordance data. For example, in the ERT protocol, when the system 100 detects that the ventilator mode has been changed, and this is used to detect the start of an ERT protocol and triggers dynamic concordance tracking for the protocol.

After the course of action for the protocol is initiated, the concordance module 110 may continue to communicate with the same, different, or additional sensors 102 to determine patient 101 compliance with the protocol. The compliance module 110 may determine the compliance of the patient 101 with the medical protocol as a function of newly received patient data and the compliance rules in the library 108. Compliance is generally determined as a calculation of whether the patient data meets acceptable levels set by the library 108 for the particular protocol (e.g., the patient variable is compared to the level or range required by the library 108). Additionally, the compliance module 110 may visually indicate (e.g., via the user interface 112) the real-time patient dynamic concordance status. FIG. 4 schematically shows eligibility rules 122 and compliance rules 124 for an example of an extubation readiness test protocol in accordance with illustrative embodiments. It should be understood that the tracked parameters for eligibility may differ from the tracked parameters for compliance, as shown in FIG. 4. The concordance module 110 may send the dynamic concordance rate to the user interface 112, which displays the dynamic concordance rate. Accordingly, the attention of the medical practitioner may be drawn to the patient in need of action.

The quality reporting module 114 may track a dynamic concordance rate as a percentage of time over which the patient 101 is compliant with the medical protocol and/or the patient eligibility time. Additionally, the quality reporting module 114 may retrospectively look at patient concordance rate and/or eligibility time to see how well a particular patient and/or patients of a particular medical practitioner have performed relative to a patient population. Additionally, the reporting module 114 may be configured to display the received patient data and to mark non-compliant portions of the received data. Thus, the quality reporting module 114 allows medical facilities and/or staff to evaluate how well patients were managed retrospectively. For example, if eligibility times are very high, medical practitioners become aware of it. This assists with hospital policy formation and also with ensuring prompt action by the medical staff.

The system of FIG. 2 may include a risk-based monitoring engine 1000 (also referred to as "risk engine 1000") configured to receive data from bedside monitors 102, electronic medical records 103, treatment devices 104, and any other information that may be deemed relevant to make an informed assessment regarding the patient's clinical risks, and any combination thereof of the preceding elements.

In illustrative embodiments, the risk engine 1000 may include a physiology observer module 119 that utilizes multiple measurements to estimate probability density functions (PDF) of internal state variables (ISVs) that describe the components of the physiology relevant to the patient treatment and condition in accordance with a predefined physiology model. The ISVs may be directly observable with noise (as a non-limiting example, heart rate is a directly observable ISV), hidden (as a non-limiting example, oxygen delivery (DO2) defined as the flow of blood saturated oxygen through the aorta cannot be directly measured and is thus hidden), or measured intermittently (as a non-limiting example, hemoglobin concentration as measured from Complete Blood Count tests is an intermittently observable ISV).

In some embodiments, when the physiology observer module 119 evaluates a set of ISVs at a given time step (e.g., tk; tk+1; generally tk+n), the system 100 may not have a complete set of ISV measurements contemporaneous with that given time step. For example, the system 100 may have measurements for that given time step for some internal state variables, but may not have measurements for that given time step for some other internal state variables (e.g., a contemporaneous measurement for an intermittent ISV may not be available for the given time step). Consequently, that intermittent ISV is, for purposes of evaluating ISVs at the given time step, a hidden ISV. However, evaluation of the set of ISVs by the physiology observer module 119 (as described herein) is nevertheless possible according to embodiments described herein because the predicted PDFs of ISVs 211 carry in them the influence of past measurements of that intermittent ISV, and consequently those predicted PDFs of ISVs 211 are, in illustrative embodiments, sufficient input for the physiology observer module 119.

In one embodiment, instead of assuming that all variables can be estimated deterministically without error, the physiology observer module 119 of the present disclosure provides probability density functions as an output. Additional details related to the physiology observer module 119 are provided herein.

The clinical trajectory interpreter module 123 may be configured, for example, with multiple possible patient states, and may determine which of those patient states are probable and with what probability, given the estimated probability density functions of the internal state variables. Examples of particular patient states include, but are not limited to, hypotension with sinus tachycardia, hypoxia with myocardial depression, compensated circulatory shock, cardiac arrest, hemorrhage, amongst others. In addition, these patient states may be specific to a particular medical condition, and the bounds of each of the patient states may be defined by threshold values of various physiological variables and data. In various embodiments, the clinical trajectory interpreter module 123 may determine the patient conditions under which a patient may be categorized using any of information gathered from reference materials, information provided by health care providers, other sources of information.

The reference materials may be stored in the database 105 or other storage device that is accessible to the risk-based monitoring application 1020 via network interface 113, for example. These reference materials may include material synthesized from reference books, medical literature, surveys of experts, physician provided information, and any other material that may be used as a reference for providing medical care to patients. In some embodiments, the clinical trajectory interpreter module 123 may first identify a patient population that is similar to the subject patient being monitored. By doing so, the clinical trajectory interpreter module 123 may be able to use relevant historical data based on the identified patient population to help determine the possible patient states.

The clinical trajectory interpreter module 123 is capable of also determining the probable patient states under which the patient can be currently categorized, given the estimated probability density functions of the internal state variables, as provided by physiology observer module 122. In this way, each of the possible patient states is assigned a probability value from 0 to 1. The combination of patient states and their probabilities is defined as the clinical risk to the patient.

Each of the above-described components is operatively connected by any conventional interconnect mechanism. FIG. 2 simply shows a bus communicating each of the components. Those skilled in the art should understand that this generalized representation can be modified to include other conventional direct or indirect connections. Accordingly, discussion of a bus is not intended to limit various embodiments.

Indeed, it should be noted that FIG. 2 only schematically shows each of these components. Those skilled in the art should understand that each of these components can be implemented in a variety of conventional manners, such as by using hardware, software, or a combination of hardware and software, across one or more other functional components. For example, the quality reporting module 114 may be implemented using a plurality of microprocessors executing firmware. As another example, the protocol eligibility and compliance module 110 may be implemented using one or more application specific integrated circuits (i.e., "ASICs") and related software, or a combination of ASICs, discrete electronic components (e.g., transistors), and microprocessors. Accordingly, the representation of the components in a single box of FIG. 2 is for simplicity purposes only.

In some embodiments, components of the system may be separated into different components. For example, the protocol eligibility and compliance module may be split into two different modules, e.g., a protocol eligibility module and a protocol compliance module. Additionally, various components, such as the sensor/medical device interface 106 of FIG. 2, may be distributed across a plurality of different machines—not necessarily within the same housing or chassis.

Additionally, in some embodiments, components shown as separate (such as the eligibility and compliance module 110 and the quality reporting module 114 in FIG. 2) may be replaced by a single component. Illustrative embodiments may include additional modules not explicitly shown here. Furthermore, certain components and sub-components in FIG. 2 are optional. For example, some embodiments may not include the protocol trigger module 116.

It should be reiterated that the representation of FIG. 2 is a significantly simplified representation of the system 100. Those skilled in the art should understand that such a device may have other physical and functional components, such as central processing units, other packet processing modules, and short-term memory. Indeed, the system 100, in various embodiments, includes one or more of the following: a processor, a memory coupled to the processor, and a network interface configured to enable the system to communicate with other devices over a network. In addition, the system may include a risk-based monitoring application 1020 that may include computer-executable instructions, which when executed by the processor 111, cause the system to be able to afford risk-based monitoring of the patients, such as the patient 101. Accordingly, this discussion is not intended to suggest that FIG. 2 represents all of the elements of the system 100.

Figure 5:
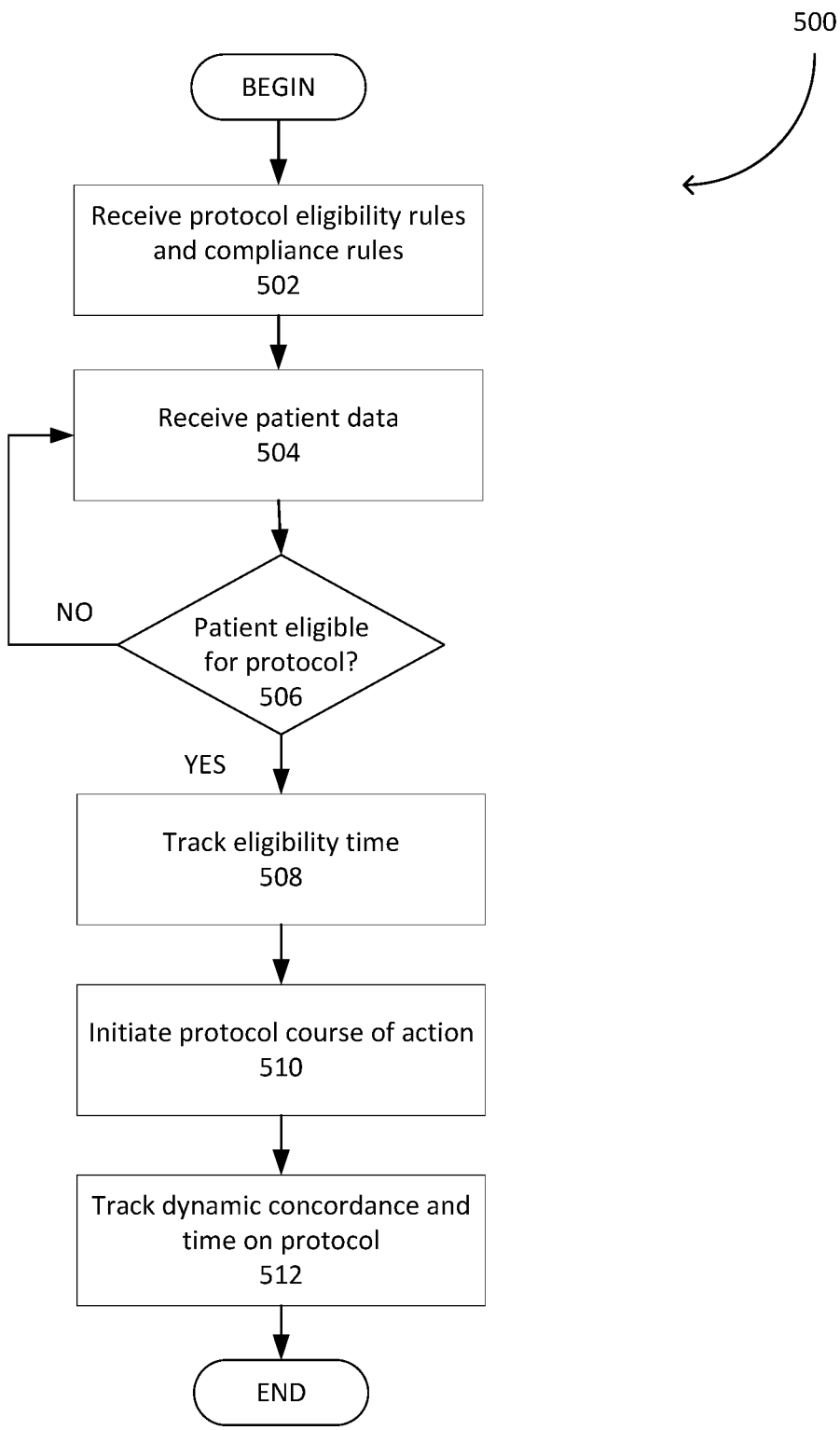
FIG. 5 shows a process of determining that the patient is eligible for the medical protocol in accordance with illustrative embodiments.

FIG. 5 shows a process 500 of determining that the patient 101 is eligible for the medical protocol. It should be noted that this process can be a simplified version of a more complex process that may normally be used. As such, the process may have additional steps that are not discussed. In addition, some steps may be optional, performed in a different order, or in parallel with each other. Accordingly, discussion of this process is illustrative and not intended to limit various embodiments of the invention. Finally, although this process is discussed with regard to entering a single patient in a medical protocol, the process of FIG. 5 can be expanded to cover processes for entering a plurality of patients in one or more medical protocols at the same time. Accordingly, the process 500 is merely exemplary of one process in accordance with illustrative embodiments of the invention. Those skilled in the art therefore can modify the process as appropriate.

The process begins at step 502, which receives eligibility rules and compliance rules for one or more protocols. In illustrative embodiments, the eligibility rules and compliance rules are received from the medical protocol library 108. As described previously, the protocol library 108 contains information relating to a plurality of medical protocols.

FIG. 6 schematically shows a generic example of a medical protocol 120 having a variety of eligibility rules 122, compliance rules 124, a protocol trigger 126, subscription rules 128, and notification rules 130 in accordance with illustrative embodiments. Although the eligibility rules 122, the compliance rules 124, the protocol trigger 126, subscription rules 128, and the notification rules 130 are shown as being part of a single protocol 120, in some embodiments, the protocol eligibility rules 122, the compliance rules 124, the protocol trigger 126, subscription rules 128, and/or the notification rules 130 may be received at different times within the process 500 of FIG. 5. Additionally, in some embodiments, the medical protocol 120 may not include subscription rules 128, the notification rules 130, the compliance rules 124 and/or the protocol triggers 126.

The eligibility rules 122 may include one or more conditions that must be satisfied (e.g., true or false) for the patient 101 to be eligible for the protocol 120. The eligibility module 110 may compare data in the database 105 and/or EMR 103 with the rules 122 to determine whether the rules 122 are met. Additionally, or alternatively, the eligibility rules 122 may include one or more parametric conditions that must be satisfied (e.g., a certain variable is greater than a particular value). The eligibility module 110 may receive patient data 106 from the interface 106 to determine whether the patient 101 is eligible (e.g., the rules 122 are satisfied).

In a similar manner, the compliance rules 124 may include a variety of conditions that must be satisfied (e.g., true or false) for the patient 101 to be in compliance with the protocol 120. The compliance module 110 may compare data in the database 105 and/or EMR 103 with the rules 122 to determine whether the rules 122 are met. Additionally, or alternatively, the compliance rules 124 may include a variety of parametric conditions that must be satisfied (e.g., a certain variable is greater than a particular value). The compliance module 110 may receive patient data 106 from the interface 106 to determine whether the patient is in compliance with the protocol 120 (e.g., the rules 124 are satisfied).

Furthermore, in some embodiments the protocol 120 may define a protocol trigger 126 that includes one or more conditions that automatically trigger the course of action to begin when satisfied. In some embodiments, the conditions may include a dynamic concordance rate of the given protocol or of a parent protocol. The protocol trigger module 116 may detect when these conditions are satisfied, and may communicate with and/or control one or more medical devices 104 to begin the course of action. Additionally, or alternatively, the protocol trigger module 116 may receive an indication (e.g., from a medical device 104 or from a medical practitioner through the user interface) that instructs the protocol trigger module 116 to activate the compliance module 110. The compliance module 110 then begins to track dynamic concordance.

In various embodiments, the protocol 120 may further include subscription rules 128 and notification rules 130. The subscription rules 128 assign different subscription levels to different medical practitioners. For example, the direct care team may be subscription level 1, whereas the management team by may be subscription level 2. The subscription rules 128 may be used in the notification rules 130. Accordingly, different subscriptions may receive different notifications and/or notifications for different reasons.

The process then proceeds to step 504, which receives patient data directly or indirectly. The patient data may be received directly (e.g., streamed) in real-time from the sensors 102 and/or medical devices. The patient data may include internal state variables (or "ISV"), which are parameters of the patient's physiology that is physiologically relevant to treatment and/or a condition of a patient. ISVs may be directly observable with noise (as a non-limiting example, heart rate is a directly observable ISV), hidden (as a non-limiting example, oxygen delivery (DO2) defined as the flow of blood saturated oxygen through the aorta cannot be directly measured and is thus hidden), or measured intermittently (as a non-limiting example, hemoglobin concentration as measured from Complete Blood Count tests is an intermittently observable ISV). Other examples of ISVs include, without limitation, Pulmonary Vascular Resistance (PVR); Cardiac Output (CO); hemoglobin, and rate of hemoglobin production/loss.

Additionally, in some embodiments, the relevant patient data may be indirectly received (e.g., may not be directly observable/measurable). A hidden Internal State Variable, means an ISV that is not directly measured by the sensor 102 coupled to the patient 101. Some hidden ISVs cannot be directly measured by the sensor. In some embodiments, the module may receive, in addition to or instead of sensor data, data representing a risk that the patient is suffering a specific adverse medical condition as indicated by the probability of the hidden internal state variable being in a particular state. Some hidden ISVs require, for example, laboratory analysis of a sample (e.g., blood) taken from the patient. Additional details regarding hidden internal state variables are described in U.S. patent application Ser. No. 17/033,591, which is incorporated herein by reference in its entirety.

Among other things, the received patient data may include: expired CO2, end-tidal CO2 measurement (EtCO2), arterial CO2, minute ventilation, ventilator mode, drug infusion rate, respiratory rate, PaCO2 arterial blood gases, Hb Hemoglobin, HR Heart Rate, SpvO2 Pulmonary Venous Oxygen Saturation, SaO2 Arterial Oxygen Saturation, SvO2 Systemic Venous Oxygen Saturation, SpO2 Pulmonary Venous Oxygen Saturation, Mean Arterial Blood Pressure, Central Venous Pressure, Left Atrial Pressure, Right Atrial Pressure, patient weight, patient age, patient height, and/or patient medical history.

Returning to FIG. 5, the process proceeds to step 506, which determines whether the patient 101 is eligible for the protocol 120. The protocol eligibility and compliance module 110 compares the various patient data with the eligibility rules 122 to determine whether the patient 101 is eligible for the protocol 120.

FIG. 7 schematically shows an example of a medical protocol 120 for an extubation readiness trial having a variety of eligibility rules 122, compliance rules 124, and a protocol trigger 126 in accordance with illustrative embodiments. In this example, the eligibility rules 122 have three conditions: (1) FiO2 must be less than or equal to 0.5, (2) PEEP must be less than 7 cm $H_2O$, and (3) the patient must be mechanically ventilated. If any of these three conditions is not satisfied, then the process returns to step 504, which continues to receive patient data.

Alternatively, if the eligibility rules 122 are satisfied, then the process optionally proceeds to step 508, which tracks the eligibility time. In illustrative embodiments, the quality reporting module 114 tracks the time at which the patient 101 became eligible for the protocol 120, and the duration from the eligibility time to a predetermined event. The predetermined event may be, for example, when a medical practitioner acknowledges patient eligibility (e.g., popup notification on touch screen display via user interface 112), or when the course of action for the eligible protocol is initiated. FIG. 3 schematically shows a popup notification on the touch screen indicating that the user is ready to start the protocol. Additionally, or alternatively, the system 100 can automatically detect received data from a peripheral device associated with the course of action, e.g. a mechanical ventilator, and determine that the medical practitioner has initiated the course of action associated with the protocol, (e.g. the ventilator setting has been transitioned).

The process then proceeds to step 510, which initiates the course of action associated with the protocol (also referred to as entering the patient 101 into the protocol). In some embodiments, the course of action is automatically entered into by the system 100, which controls a medical device 104. Accordingly, because the protocol 120 is automatically triggered, step 508 may be skipped (e.g., because there is no time between eligibility and onset of the protocol 120). However, in some other embodiments, an indication (e.g., notification or alert) is provided to the medical practitioner (e.g., via the user interface) that the patient 101 is eligible for the course of action. The medical practitioner may initiate the course of action by approving (e.g., through the user interface) the automatic initiation of the course of action by the system, or by manually initiating the course of action. The patient 101 then enters the protocol 120. For example, the patient 101 may be entered into the extubation readiness trial protocol 120. In some embodiments, the protocol 120 may include the trigger 126 that automatically enters the patient 101 into the protocol 120.

After the course of action is initiated, the protocol trigger module 116 communicates with the compliance module 110 to begin tracking patient compliance with the protocol 120. In some embodiments, the trigger 126 automatically activates the compliance module 110. Alternatively, the protocol trigger module 116 is instructed by the medical practitioner (e.g., through approval or manual input to the user interface) to instruct the compliance module to begin tracking data.

The process then proceeds to step 512, which tracks the dynamic concordance of patient 101. As mentioned previously, dynamic concordance rate is the rate at which patient physiological data is consistent with the compliance rules 124 of the protocol. As shown in the example of FIG. 7, the protocol 120 may include one or more compliance rules 124. In the example of FIG. 7 the compliance rules include: (1) SpO2 is greater than 88%, (2) Tidal Volume is greater than 5 ml/kg, (3) (EtCo2-EtCo2@ baseline)/EtCO2@baseline is less than 1.2, (4) (HR-HR@baseline)/HR@baseline is less than 1.2, and (5) the patient is on pressure support ventilation. If any of these conditions is not satisfied, then the entire protocol 120 may be said to be not in compliance. The quality reporting module 114 tracks the duration and times during which the protocol 120 is not in compliance to determine the dynamic concordance rate.

For the sake of an example, the calculation of a dynamic condition such as heart rate at baseline is described. When the protocol is triggered, either manually or automatically, the system 100 takes the average of the measure in some period leading to the trigger. This period may be, for example, over 1 minute, 1 hour, or 2 hours prior to the trigger. In various embodiments, this average constitutes the baseline. The medical practitioner receives the baseline computed by the system 100 (e.g., via the user interface 116) and may adjust the baseline value given the provider's preference or the patient condition specifics (e.g., via the user interface 116). In various embodiments, the system 100 may track various patient parameters for a pre-determined time and automatically compute patient baseline parameters.

In some embodiments, the system 100 determines that the patient 101 is below a threshold concordance rate for the protocol 120. The system 100 may provide an indication (e.g., through a notification or alert) to the medical practitioner that the patient is below the threshold concordance rate, and/or that dynamic concordance is trending downward. The indication prompts the medical practitioner to check on or reevaluate the patient 101 to identify and mitigate reasons for non-compliance.

The medical practitioner may then review the longitudinal data in the user interface 116 and diagnose the reasons for noncompliance. If appropriate and possible, the medical practitioner may take an intervening action to cause the dynamic concordance rate to increase. As a nonlimiting example, a patient under care for Acute Respiratory Distress Syndrome may be ventilated according to a protocol requiring Tidal Volume less than 7 ml/kg and peak inspiratory pressure less than 30 mm Hg. A decreasing concordance rate indicates that one of these conditions is not met. The system 100 sends a notification to the medical practitioner informing them of the decreasing concordance rate. The practitioner can review that data to identify which condition is not met, and adjust the ventilation setting to provide optimal ventilation with lower risk for lung injury and respective better expected patient outcome.

Figure 8:
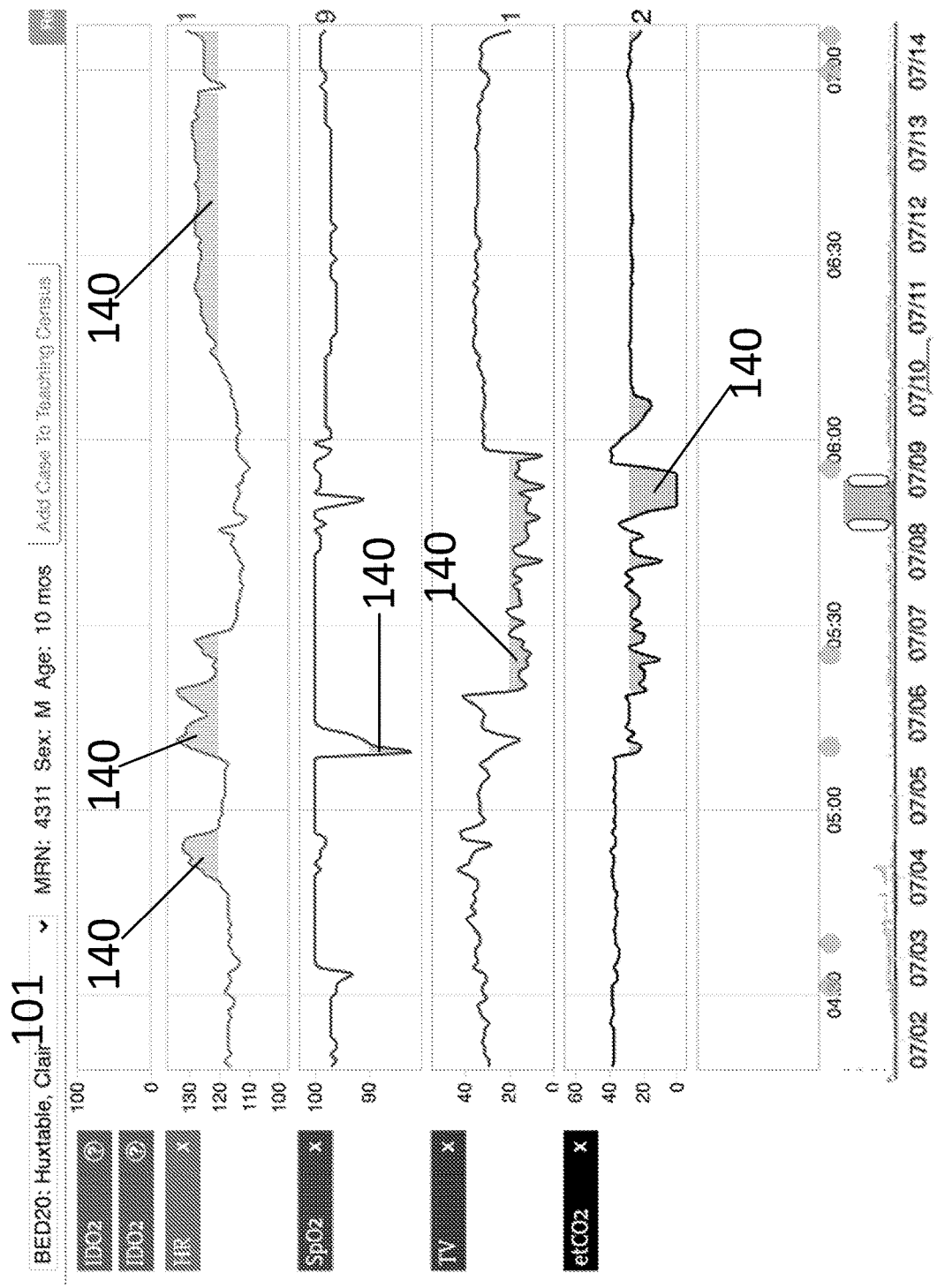
FIG. 8 shows a user interface for tracking compliance with the protocol in accordance with illustrative embodiments.

FIG. 8 shows a user interface for tracking compliance with the protocol 120. The plurality of patient data tracked in real-time is shown for the patient 101. In the example of FIG. 8, HR, SpO2, TV, and etCO2 are tracked. Illustrative embodiments may track compliance at the parameter level. Furthermore, the user interface 112 may be configured to display non-compliant periods 140 (e.g., represented by shaded areas of the patient data).

Figure 9:
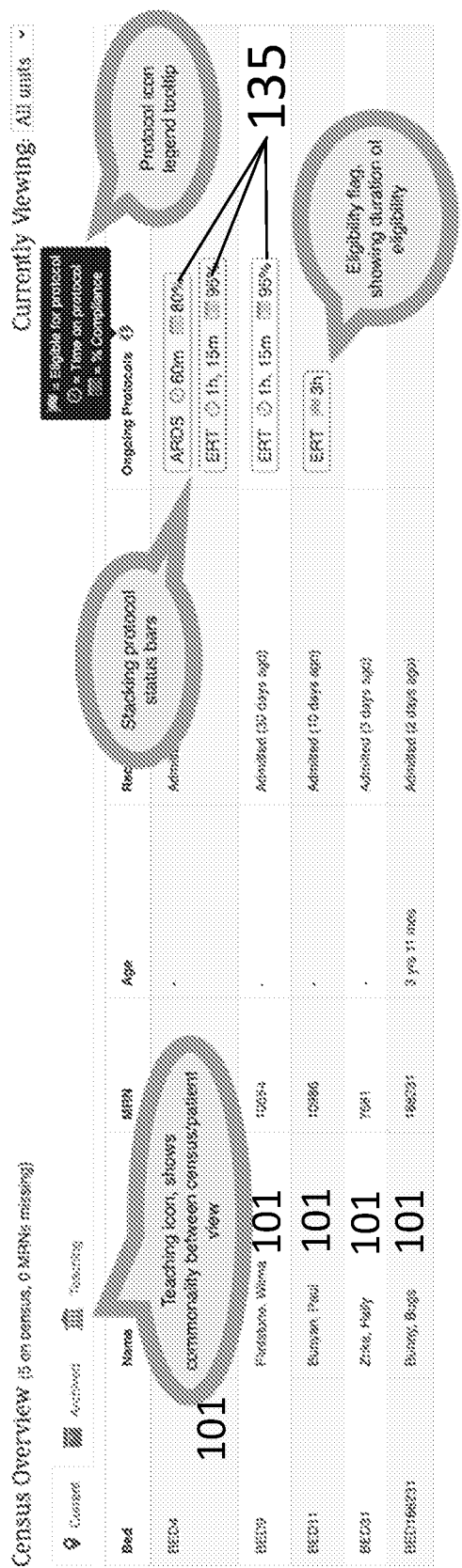
FIG. 9 schematically shows an interface for showing protocol compliance and time on protocol for a plurality of patients in accordance with illustrative embodiments.

FIG. 9 schematically shows an interface for showing protocol compliance and time on protocol 120 for a plurality of patients 101 in accordance with illustrative embodiments of the invention. As shown, some patients 101 may be eligible or actively engaged in one or more protocols (e.g., ARDS and ERT protocols 120). Additionally, the interface 112 may show protocol duration (e.g., 1 hour and 15 minutes for Flintstone, Wilma) as well as eligibility duration (e.g., 3 hours for Bunyan, Paul). The interface may also show the overall concordance rate for completed and/or active protocols.

Figure 10:
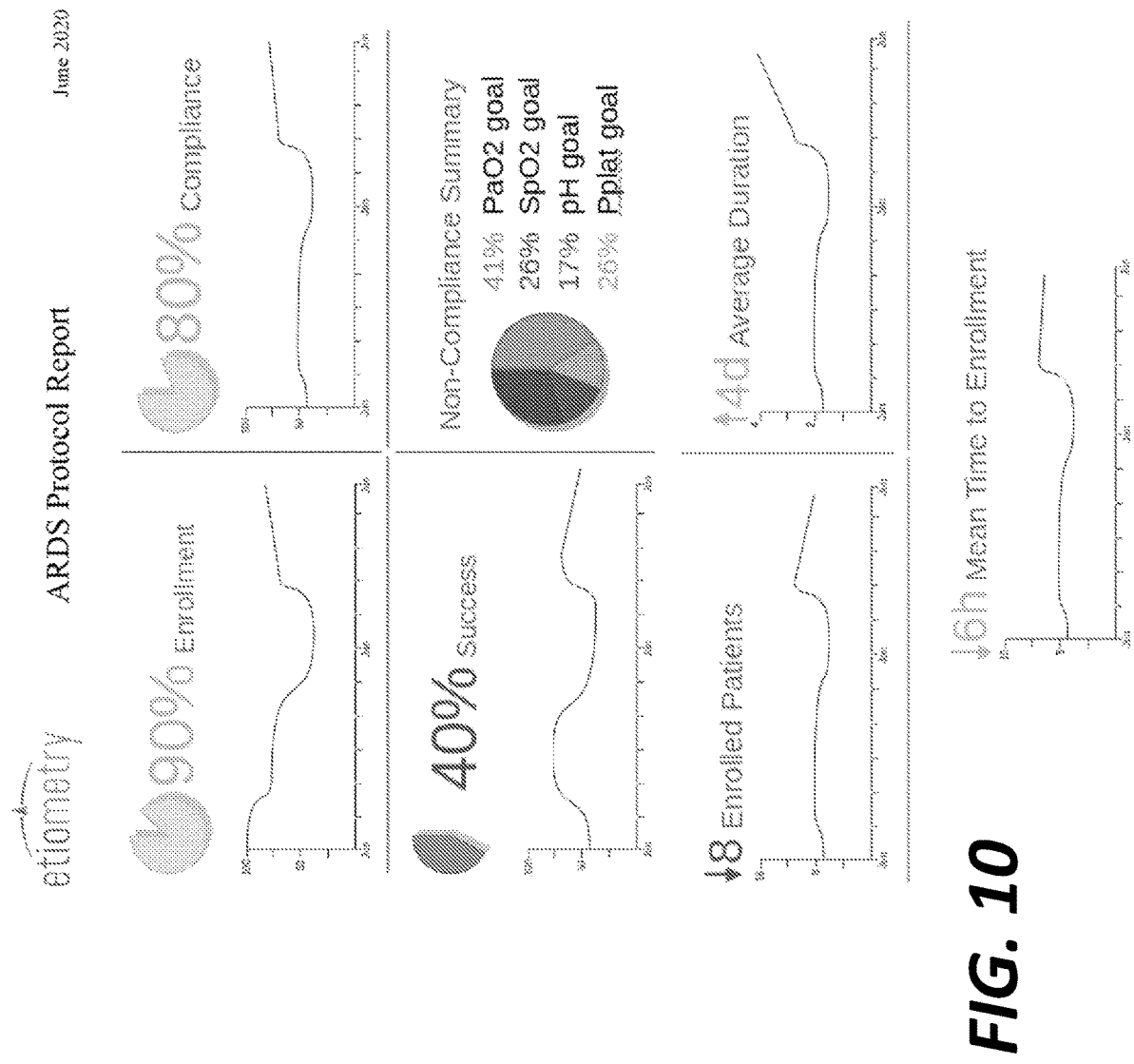
FIG. 10 schematically shows a report generated by the quality reporting module showing facility wide compliance with protocols in accordance with illustrative embodiments of the invention.

Illustrative embodiments may provide periodic reporting to assist medical practitioners with understanding facility wide compliance. FIG. 10 schematically shows a report generated by the quality reporting module 114 showing facility wide compliance with protocols in accordance with illustrative embodiments of the invention. The report may include information relating to the percentage of eligible patients that are enrolled in the protocol, the overall compliance, the success rate, the number of enrolled patients over time, a summary of the parameters that led to non-compliance, the average duration of compliance, and the mean time to enrollment, among other things. Accordingly, the information in the report may be used to help improve patient 101 treatment over time, and also to let the medical practitioner track what areas/parameters need to be monitored more closely for optimal clinical outcomes. After the protocol is completed (e.g., the patient is successfully extubated) or otherwise concluded, the process 500 then comes to an end.

Although not explicitly shown in the process 500 of FIG. 5, it should be understood that throughout the process notifications may be provided to relevant medical staff. To that end, the patient tracking module 118 may receive the subscription rules 128 and the notification rules 130, as well as patient status information from the protocol eligibility and compliance module 110. As the rules 130 are met, the tracking module 118 sends a notification to the various subscribed users in accordance with their subscription level. For example, notifications may be sent when eligibility status is changed, when the course of action begins (also referred to as protocol enrollment), and/or when the patient is out of compliance.

Furthermore, different subscription levels may receive different notification types. For example, "notification 1" may include a passive notification, such as an alert through the user interface 112; "notification 2" may include an escalated passive notification, such as a text and/or an email; and "notification 3" may include an active notification such as paging the medical staff.

Subscription rules 128 may be protocol based. Accordingly, a particular medical practitioner may be subscribed to notifications for all patients 101 on a particular protocol. Additionally, or alternatively, subscriptions may be patient-based. Patient-based subscribers receive notifications relating to any and all protocols associated with a given patient 101. Illustrative embodiments also allow the medical practitioner to manually adjust or create notification protocols that are not limited to protocol based or patient-based notifications.

Illustrative embodiments may communicate with a scheduling system (e.g., hospital scheduling system) to determine which patient is under the care of which medical practitioner, and other information relating to the medical practitioner (e.g., unit, work schedule data, medical specialties, etc.). For example, the system may receive data indicating that patient John Smith may be under the care of bedside nurse Jackey, intensivist Dr Smith, and respiratory therapist Johnson. Accordingly, the notification system may receive appropriate information regarding who to notify in accordance with the subscription rules 128.

Nested Protocols

Figure 11:
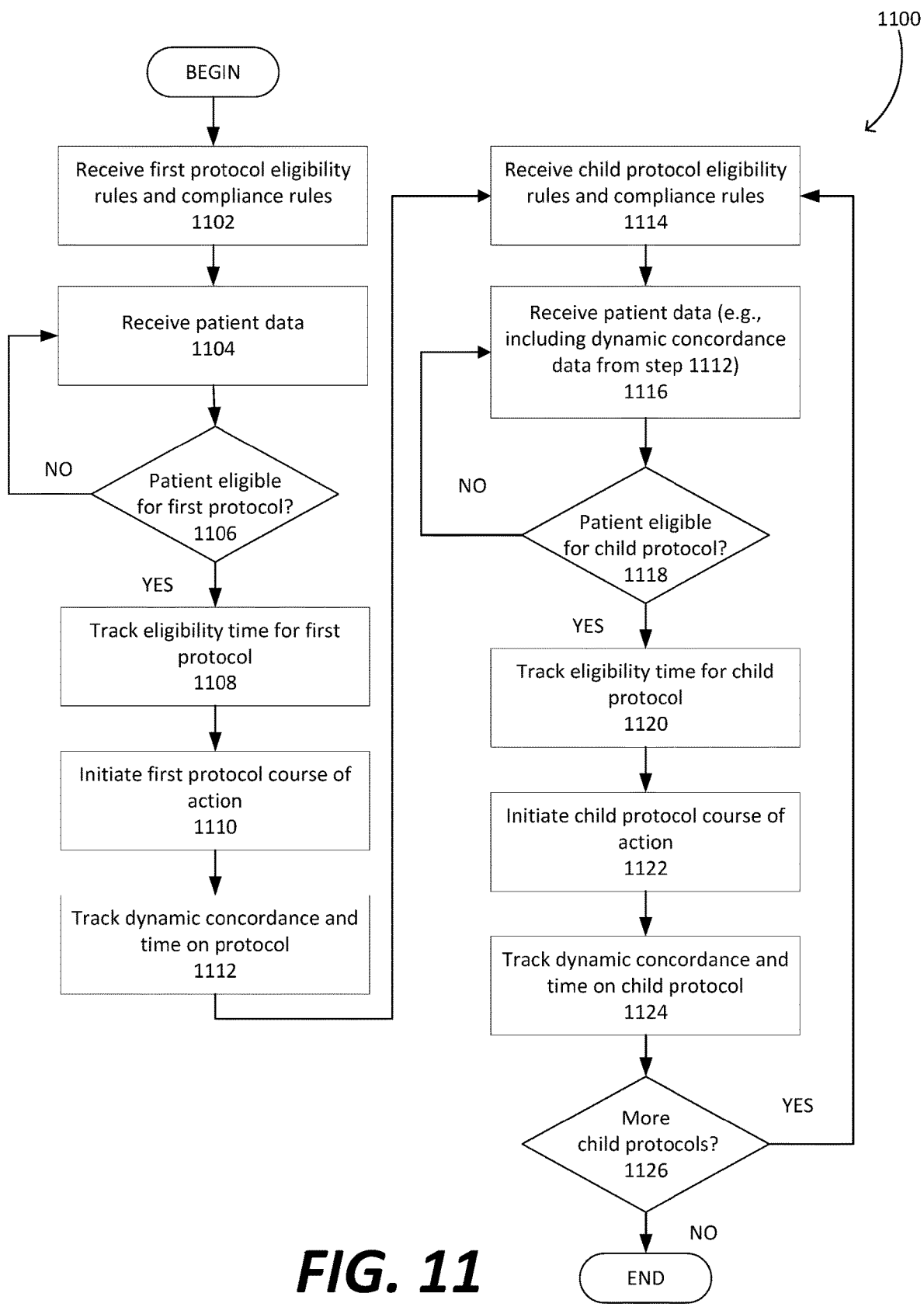
FIG. 11 shows a process of nesting protocols in accordance with illustrative embodiments.

FIG. 11 shows a process 1100 of nesting protocols in accordance with illustrative embodiments of the invention. It should be noted that this process can be a simplified version of a more complex process that may normally be used. As such, the process may have additional steps that are not discussed. In addition, some steps may be optional, performed in a different order, or in parallel with each other. Accordingly, discussion of this process is illustrative and not intended to limit various embodiments of the invention. Finally, although this process is discussed with regard to entering a single patient in a medical protocol, the process of FIG. 11 can be expanded to cover processes for entering a plurality of patients in one or more medical protocols at the same time. Accordingly, the process 1100 is merely exemplary of one process in accordance with illustrative embodiments of the invention. Those skilled in the art therefore can modify the process as appropriate.

Steps 1102-1112 are substantially the same as steps 502-512 of FIG. 5, respectively, and therefore, discussion of these steps is not again repeated in great detail. Steps 1102-1112 generally describe a process of determining whether a patient is eligible for a first protocol, and tracking the dynamic concordance rate of the patient after a course of action of the protocol begins.

FIG. 12 schematically shows an example of nested medical protocols having a variety of eligibility rules, compliance rules, and a protocol trigger in accordance with illustrative embodiments. As shown in the example of FIG. 12, the eligibility rules 122 of the ventilation weaning protocol 120B are dependent upon a particular outcome from the ventilation protocol 120A. For the sake of discussion, the dependent protocol 120E may be referred to as the child protocol 120B. Whereas the protocol 120A, upon which the child protocol 120B depends, may be referred to as a parent protocol 120A. Despite the use of this nomenclature, it should be understood that a child protocol 120B may itself in turn be a parent protocol for a different protocol (e.g., a third protocol 120C). Furthermore, although not shown in this example, a child protocol 120B may have multiple parent protocols 120A upon which it depends. In a similar manner, a parent protocol may have multiple child protocols, with each child triggered by different conditions associated with the parent protocol (e.g., different dynamic concordance rates may trigger different child protocols).

In a manner similar to the previously described protocol 120 of FIG. 6, each of the protocols 120A-120C in FIG. 12 has a respective set of eligibility rules 122, a course of action or trigger 126, and compliance rules 124. In the process of FIG. 11, steps 1102-1112 may relate to, for example, the first protocol 120A.

At step 1110, the course of action (e.g., ventilation) begins when the eligibility rules 122 of the first protocol 120A are satisfied. After the course of action begins, the dynamic concordance rate for the various compliance rules 124 is tracked at step 1112.

Step 1114 receives the eligibility rules 122 and the compliance rules 124 for the second protocol 120B. Although step 1114 is shown as occurring after step 1112, in practice, this step may occur earlier in the process 1100 (e.g., simultaneously with 1102).

At step 1116, the process receives patient data, which includes the dynamic concordance rate of the first protocol 120A (also referred to as the parent protocol). At step 1118, the process 1100 determines if the patient is eligible for the second protocol. Step 1118 compares the received data from step 1116 with the eligibility rules 1222 for the protocol 120B. Among other things, the eligibility rules 122 for the child protocol 120B (the nested protocol) may include the dynamic concordance rate from another protocol (e.g., the parent protocol 120A). In illustrative embodiments, the system 100 enables the use of nested protocols by keeping track of the status of each protocol 120A-120C and continuously calculating dynamic concordance rate.

In the example of FIG. 12, the second protocol 122 requires a 90% or greater dynamic concordance for more than 3 hours for the ventilation protocol 120A. The system 100 tracks all of the relevant data relating to the compliance 124 of the first protocol 120A, and calculates the dynamic concordance rate. Although the eligibility rules show a reliance only on a single parent protocol (i.e., the ventilation protocol 120A), it should be understood that eligibility rules 122 for a protocol may include dynamic concordance rates (or other variables) from multiple other protocols. Thus, a single child protocol 120B may have multiple parent protocols 120A.

Additionally, illustrative embodiments enable the use of various nested eligibility rules 122 and/or compliance rules 124. For example, rules 122 and 124 may rely on an overall dynamic concordance rate for one or more parent protocols 120A, a dynamic concordance rate for a most recent period of time (e.g., 90% or greater for the most recent 3 hours) for the one or more parent protocols 120A, a total minimum time above threshold dynamic concordance rate (e.g., 2 hours above threshold, 1 hour below threshold, and 1 hour above threshold), and/or a dynamic concordance rate that is a function of a plurality of parent protocols 120A (average dynamic concordance rate for plurality of parent protocols 120A is above a given threshold). Various embodiments may include Boolean operators in the eligibility rules 122 and/or the compliance rules 124 (e.g., "and," "or," "not").

Returning to FIG. 11, after determining that the patient 101 is eligible for the second protocol 120B, the process 1100 proceeds to step 1120, which begins tracking eligibility time for the second protocol 120B. In a manner similar to step 1108, step 1118 provides a quantitative measurement of hospital staff performance, and also provides the medical practitioner with information which may be used to prioritize the treatment of patients in the unit (and/or the medical practitioner's attention to a particular patient).

Although not explicitly shown, throughout the process of FIG. 11 notifications may be sent to medical staff in accordance with subscription rules 128 and the notification rules 130 of the protocol. For example, notifications of patient eligibility for the second protocol are sent to responsible hospital staff. Illustrative embodiments advantageously reduce unnecessary pending eligible time to initiation for patients 101 eligible for the second protocol. Furthermore, illustrative embodiments advantageously enable the user of dynamic concordance rates from the first protocol 120A as an eligibility requirement for the second protocol 120B.

The inventors believe that both of these features (i.e., reduced pending eligibility time, and focus on concordance rate based outcomes) lead to enhanced patient outcomes. The reason is that they enable the medical practitioner to provide care, which keeps the patient on the optimal progression path thus reducing time in the ICU and recovery. In the example from FIG. 11, the patient is intubated earlier by a timely notification that the patient is eligible for ventilation. The ventilation dynamic concordance rate enables the medical practitioner to longitudinally track whether the patient is receiving optimal ventilation and oxygenation, and to intervene in a timely manner if necessary. Expedited intervention reduces the risk for end-organ failure. After the patient is stabilized, the system 100 prompts the practitioner to start weaning, which effectively mitigates the risk of the patient 101 spending too much time on ventilation and experiencing ventilator associated lung injury. This further impacts the timeliness of downstream child protocols, such as the ERT protocol. The system 100 allows the clinician to know how much time the patient 101 may have been eligible for a particular protocol (e.g. the extubation trial), thus urging them to start the protocol. After the trial is completed, the system 100 provides the dynamic concordance rate to the whole clinical team during rounds or other patient care planning activity so they may timely make a decision for initiation of another protocol and/or course of action (e.g., extubation).

At step 1122, the course of action of the second protocol 120B begins (i.e., the patient 101 is enrolled in the protocol). After the second protocol 120B begins, dynamic concordance of the patient is tracked. The process then proceeds to step 1126, which asks if there are more protocols. If the answer is yes, then more patient data is received. Returning to the example of FIG. 12, a third protocol 120C has eligibility rules that relate an earlier protocol 120B. Accordingly, steps 1114-1124 are repeated for the third protocol 120C. This process may be repeated for as many protocols as necessary. Eventually, when there are no additional nested protocols, the process comes to an end.

Hidden State Variables

Various protocols 120 may include eligibility rules 122 and/or compliance rules 124 may include conditions (e.g., true or false, a certain variable is greater than a particular value, etc.) that reference hidden state variables. As described further below, these hidden state variable conditions 125 calculate a risk that a particular condition is present, as opposed to directly measuring the condition. Thus, while steps 1104 and 1116 describe receiving patient data, this patient data may also include a calculated hidden state variable which is a function of measured patient data. Details of calculating risk probabilities for certain patient conditions are described in further detail in co-pending U.S. Patent Application No. 63/091,427, which is incorporated herein by reference in its entirety.

Interface

In hospital settings it is likely that medical staff are in charge of a plurality of patients 101. There, illustrative embodiments advantageously provide an intuitive user interface for management of patient protocols by the medical practitioner.

Figure 13A:
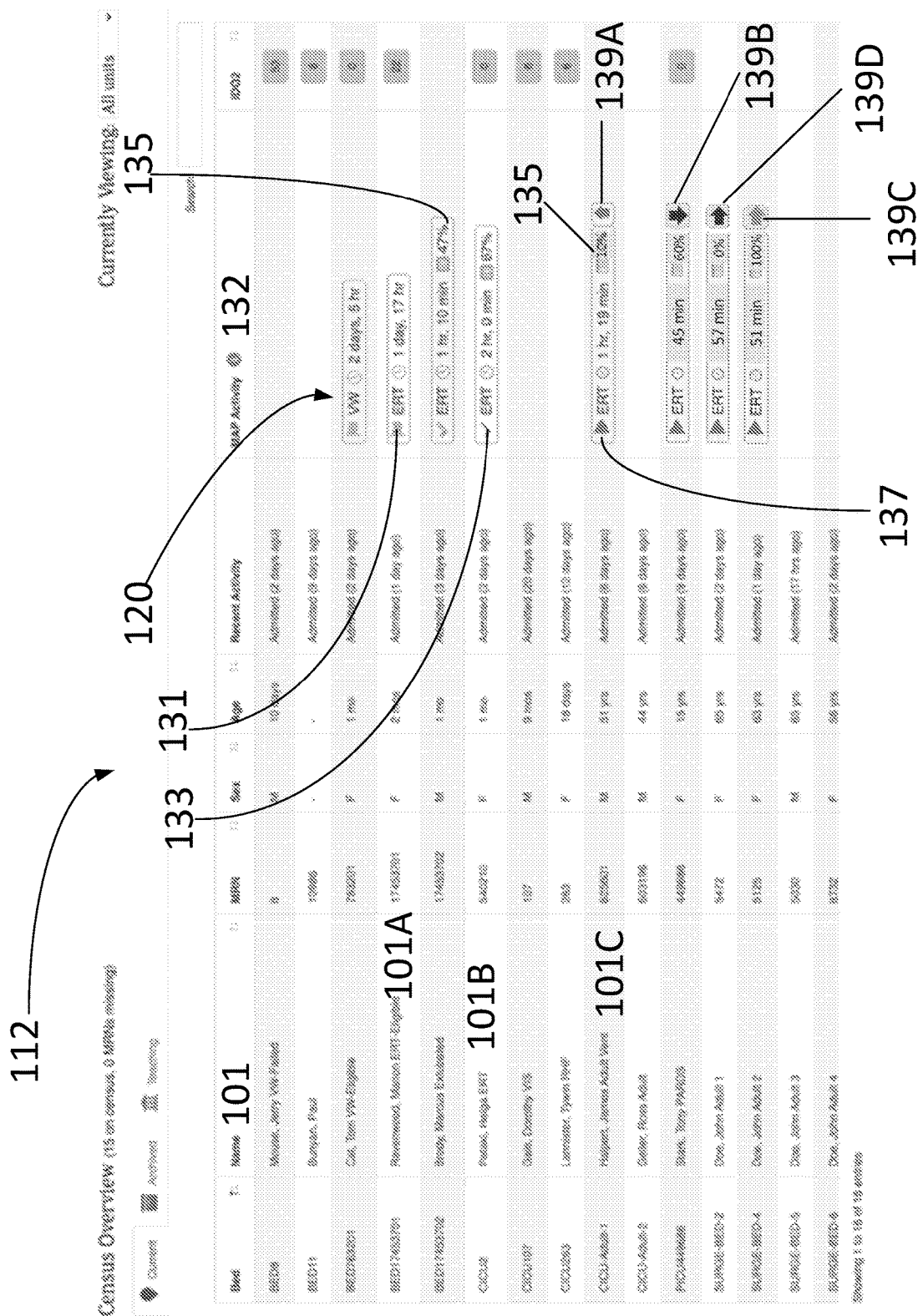

FIG. 13A schematically shows an interface 112 for viewing patient protocol 120 information in accordance with illustrative embodiments. The patient's 101 medical event history, as well as ongoing protocol, completed protocol, and/or protocol eligibility history can be viewed by the medical practitioner in the interface 112. Among other things, the interface may show the patient bed number, name, status, medical record number, sex, age, recent activity, map activity 132, and/or other parameter values.

Illustrative embodiments provide a single user interface 112 configured to display patient information relating to a plurality of patients 101. The plurality of patients 101 can be all of the patients 101 on a particular hospital floor, in a particular hospital unit, associated with a particular protocol 120, and/or under the care of a particular medical practitioner. In the same user interface 112, the protocol activity 132 for each patient 101 is shown and described. For example, patient 101A is shown as being eligible (e.g., eligibility icon 131) for an ERT protocol 120 and the eligibility time (i.e., 1 day and 17 hours for patient 101A). Patient 101B is shown as having completed an ERT protocol 120 (e.g., completed icon 133) and the total time of the completed protocol (i.e., 2 hours and 0 minutes for patient 101B). Patient 101C is shown as currently being enrolled/on-going (e.g., enrollment icon 137) in an ERT protocol 120, and the total time the patient 101C has been on the protocol (i.e., 1 hour and 19 minutes for Patient 101C).

As shown in FIG. 13A, optionally illustrative embodiments may display the amount of time the patient 101 has been or was on the protocol 120, as well as a dynamic concordance rate 135. Furthermore, illustrative embodiments may include a dynamic concordance indicator icon 139 that indicates whether the dynamic concordance rate has been trending up (e.g., green arrow icon 139A), trending down (e.g., red arrow icon 139B), or is steady within a pre-defined timeframe (e.g., horizontal green arrow 139C if the overall concordance is above a threshold or horizontal red arrow 139D if the overall concordance is below the threshold).

The system 100 may visually indicate completed protocols with a check mark on the user interface 116. These visualization enable simplify transfer of clinical care from one medical practitioner to another, and therefore, lead to better patient outcomes. For example, extubation decisions are usually made by the care team during morning rounds based on extubation readiness trials completed during the previous shift. The rounding team can review which patients have had completed ERTs and then make decision to extubate all patients with high overall concordance. The longitudinal data for patients with lower concordance can be reviewed in more detail to determine reason for noncompliance and assess whether this reason indicates unacceptable risk for extubation failure. Furthermore, in practice, by the time the protocol 120 is complete, it is possible that the medical practitioner that was in charge of the patient may have changed shifts. Illustrative embodiments provide visualizations that simplify prioritization for medical care of patients for subsequent clinicians.

Figure 13B:
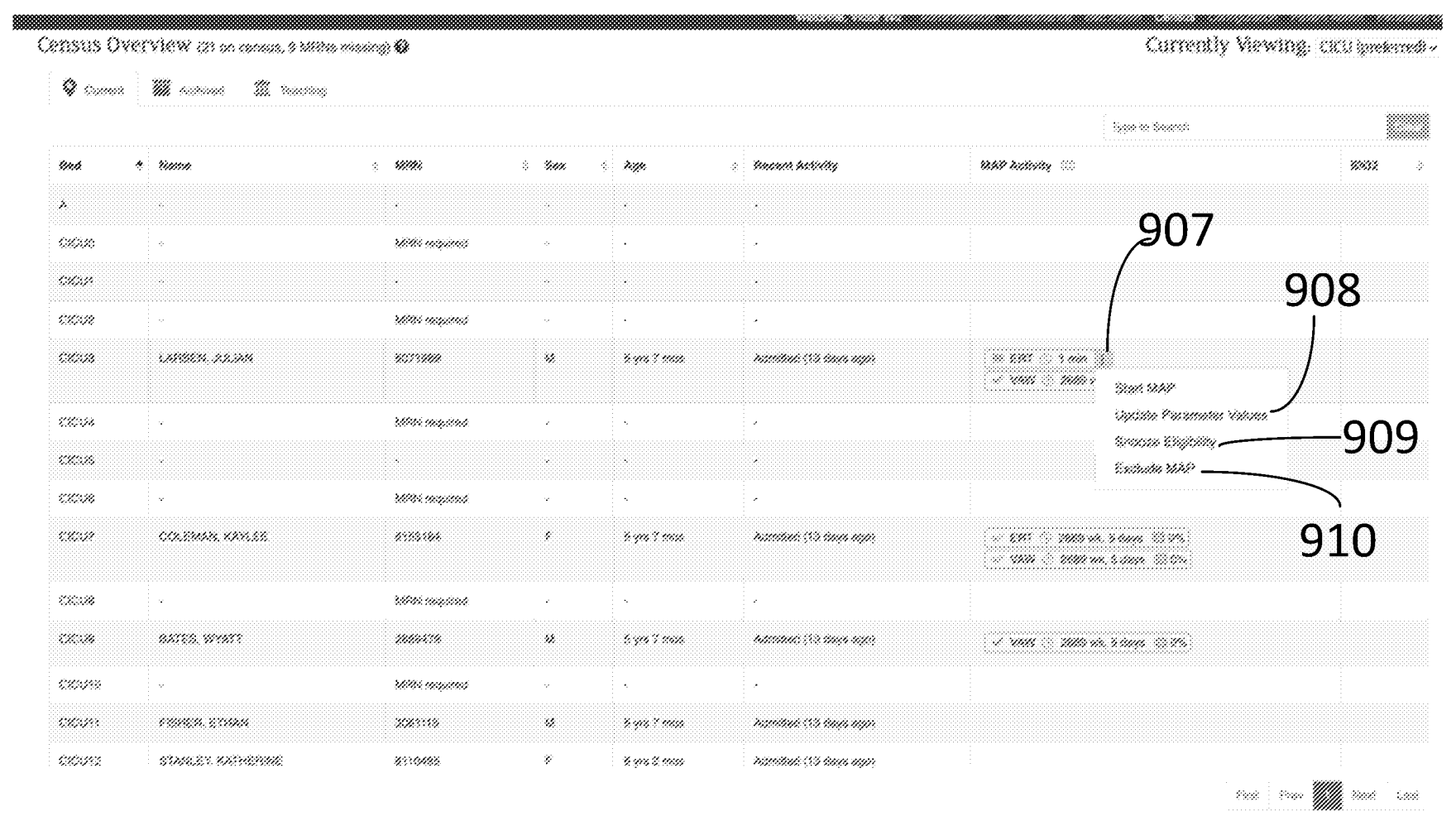

FIG. 13B schematically shows an interface 112 for viewing patient protocol 120 information in accordance with illustrative embodiments in accordance with illustrative embodiments. The interface of FIG. 13B is substantially identical to the interface of FIG. 13A, with the addition of an interface eligibility menu 907 feature having a plurality of actions related to the patient being eligible for the particular protocol. In some embodiments, the medical practitioner may manually select that the protocol has started so the system starts tracking compliance. In some other embodiments, the system may automatically detect that the user has been placed on the protocol and start tracking compliance.

The eligibility menu 907 provides a number of useful functions to the medical practitioner within the interface 112 that simplifies management and/or treatment of the patient on the protocol. For example, the menu may include an adjust parameters button 908 that provides medical practitioners with the ability to adjust the parameters related to protocol compliance and/or eligibility. The menu may also include a snooze eligibility button 909 that allows the medical practitioner to snooze eligibility (and therefore delay or stop notifications regarding eligibility and/or tracking of time since eligibility). For example, the medical practitioner may, in their medical judgment, believe that although the patient parameters are within limits, that the patient should still not be placed on the protocol. For example, the patient parameters may show that the patient is on minimal ventilation settings indicating eligibility for ERT, but physical examination may indicate that the patient does not have a coughing reflex, which leads the practitioner to snooze eligibility for a predefined period of time. Furthermore, an exclude button 910 provides medical practitioners with the ability to completely exclude a patient from a particular protocol. For example, if the patient is on chronic ventilation, the patient may not be extubated at all in that particular unit. These features help the medical staff manage notifications that may otherwise be sent and/or stop tracking inaccurate quality information.

Although the features described in FIG. 13A and 13B are shown in separate screenshots, it should be understood that all of the features discussed therein may be combined.

Figure 13C:
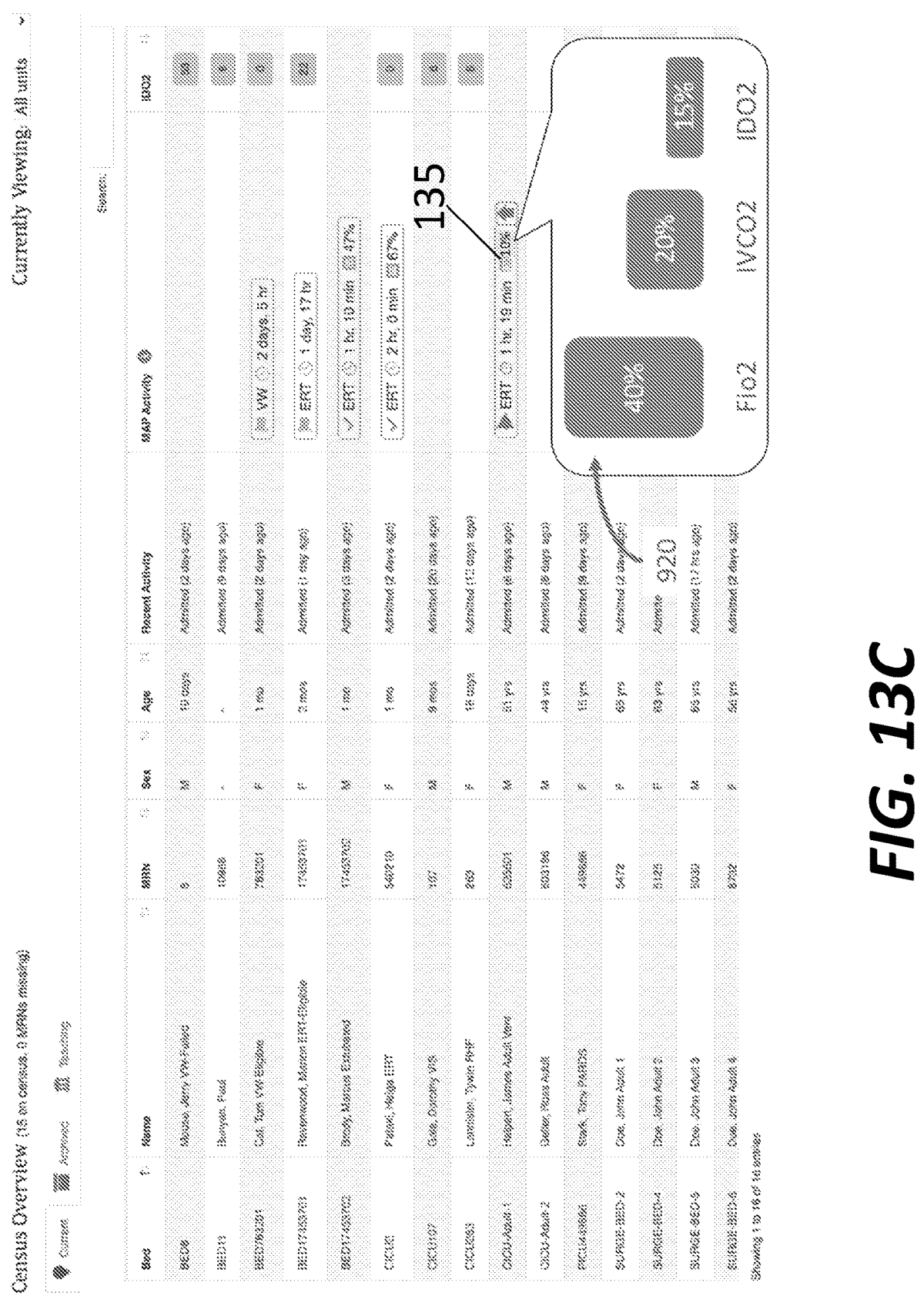

FIG. 13C schematically shows the user interface 112 of FIGS. 13A and 13B in accordance with illustrative embodiments of the invention. The medical practitioner may click on the dynamic concordance rate 135 clin to display a new compliance box 920 that the compliance of the individual parameters that determine the concordance rate. In the particular example shown, two of the parameters informing the concordance rate (IDO2 and IVCO2) are risks of hidden internal state variable being in particular states.

Figure 13D:

FIG. 13D schematically shows the protocol 120 as an overlay in the interface of FIG. 13A. A user input into the interface 112 causes the system 100 to display the eligibility rules 122 and/or the compliance rules 124 for the selected protocol 120 (e.g., user selects the protocol 120 name "ERT"). For example, the patient 101B is on an Extubation Readiness Trial. The eligibility rules 122 shown are: the patient in spontaneously breathing, PEEP<=7 cmH2O, and FiO2<=50%. The compliance rules 124 shown are: SpO2>=goal SpO2, normalized TV>5 mL/kg, RR not increased by 20% above baseline RR, and HR not increased by 20% above baseline Hr.

Returning to the census view of FIG. 13A, a user input into the interface 112 causes the system 100 to display the relevant received data for the selected protocol 120 (e.g., user selects the amount of time patient is eligible, the amount of time the patient is on the protocol, and/or the dynamic concordance rate 135).

Figure 13E:
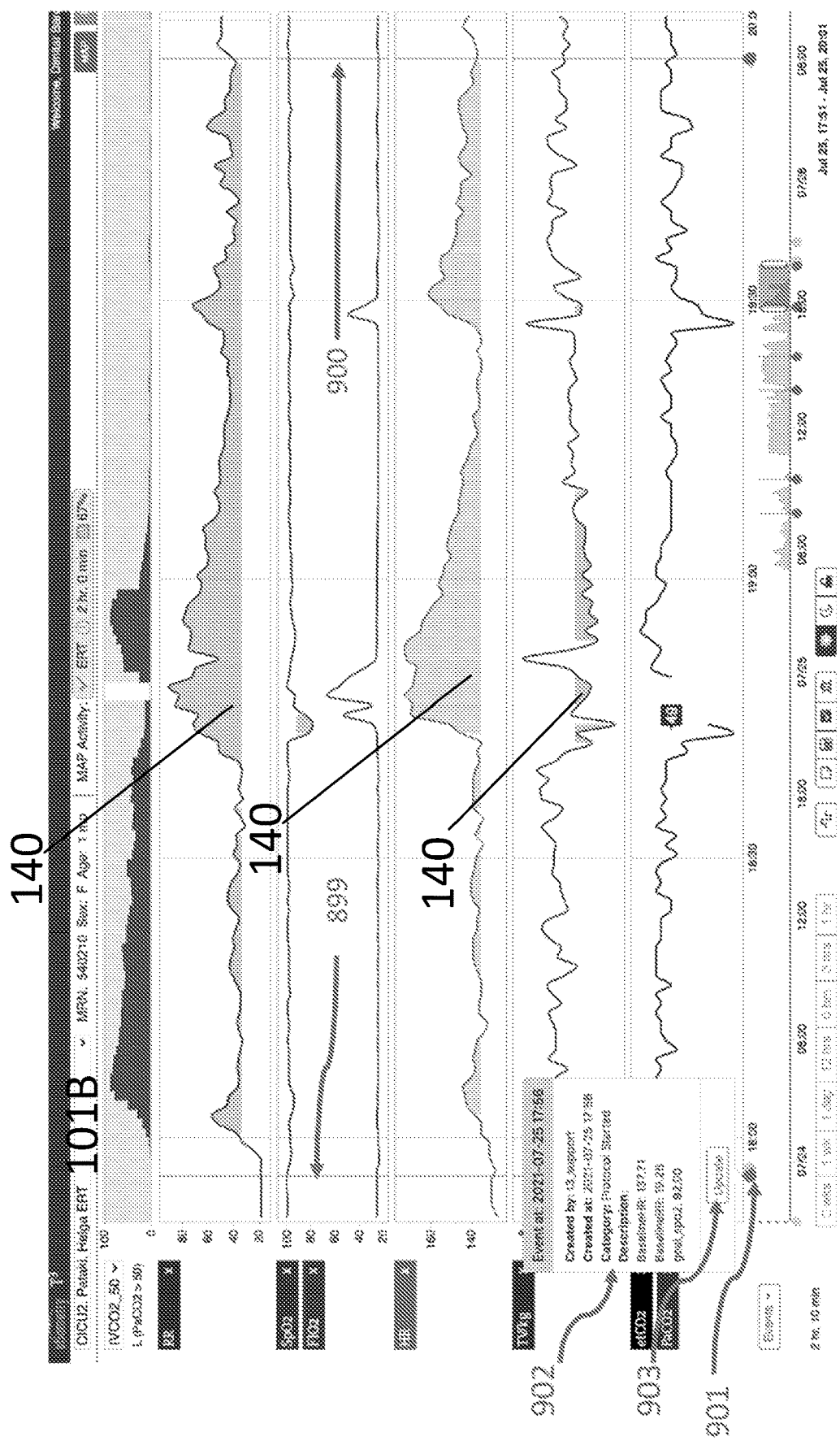

FIG. 13E schematically shows the received patient data that relates to a selected protocol 120 in FIG. 13A. Accordingly, the user interface 112 no longer shows the census view of the plurality of patients 101, but instead displays data relevant to a particular selected patient 101B. In particular, because the patient 101B has already completed the protocol 120 (e.g., ERT), the user interface 112 displays patient data relating to compliance rules 124. In a similar manner, if the patient is currently on the protocol 120, the user interface 112 displays patient data relating to the compliance rules 124. Alternatively, if the patient 101 is eligible for the protocol 120, the user interface 112 displays patient data relating to the eligibility rules 122.

The received patient data is continuously streamed (or near-continuously) streamed from the sensors 102 and/or peripheral devices 104, such that data points are collected. As shown in FIG. 13D, the example protocol has compliance rules 124 that relate to SpO2, normalized tidal volume (TV normalized in mL/kg), respiratory rate, and heart rate. Thus, the user interface 112 in FIG. 13E displays all the data that is relevant to the compliance rules 124. The user interface 112 shows non-compliant periods 140 in a visually distinguishable way (e.g., represented by shaded areas of the patient data). Advantageously, a medical practitioner may view all of the relevant patient data relating to the protocol 120 (e.g., compliance rules 124 and/or eligibility rules 122), and problematic patient data is visually emphasized. A dynamic concordance rate (e.g., 67%) is calculated that determines the amount of time the patient 101 has been in compliance over the length of the completed protocol (e.g., 2 hours). However, in ongoing protocols, the dynamic concordance rate is calculated for the time the protocol has been ongoing.

Additionally, the user interface 112 may display a protocol start indication 899 indicating the start time of the protocol relative to the displayed data. In a similar manner, illustrative embodiments may display a protocol end indication 900 indicating the end time of the protocol relative to the display data. The user interface 112 may include a user-selectable marker 901 adjacent to the protocol start indication 899. By selecting the marker 901, the interface 112 displays a text box 902 that has information relating to the exact time of the protocol and/or the computed baselines at the beginning of the protocol (e.g., against which the patient 101B is evaluated). If desired, the medical practitioner can select an update icon 903 to update the baselines either before, during, or after the protocol.

Figure 13F:
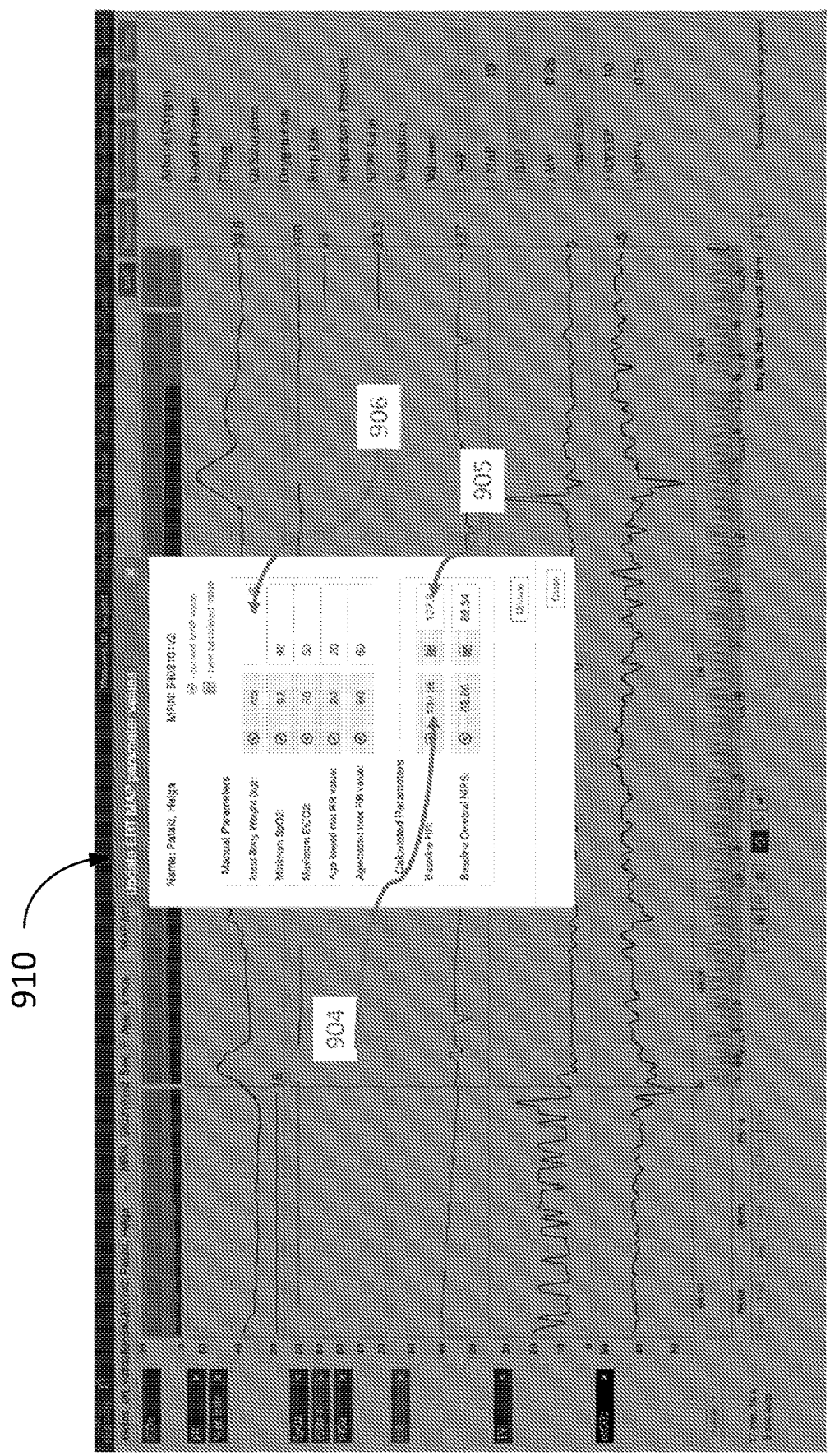

FIG. 13F schematically shows an overlay window 910 that displays in the user interface 112 when the update icon 903 is selected in accordance with illustrative embodiments. A baseline heartrate 904 is automatically calculated based on the average of a time period (e.g., 1 minute, 2 minutes, 1 hour, or 2 hours) before the start of the protocol 120. This sets the baseline parameter. However, overwrite box 905 allows a medical practitioner to overwrite these parameters and put in new parameters (e.g., if the practitioner believes that a protocol 120 using a baseline parameter has a baseline that is not sufficient for the protocol 120). Furthermore, other parameters 906 may be manually entered or overwritten by a medical practitioner.

Figure 13G:
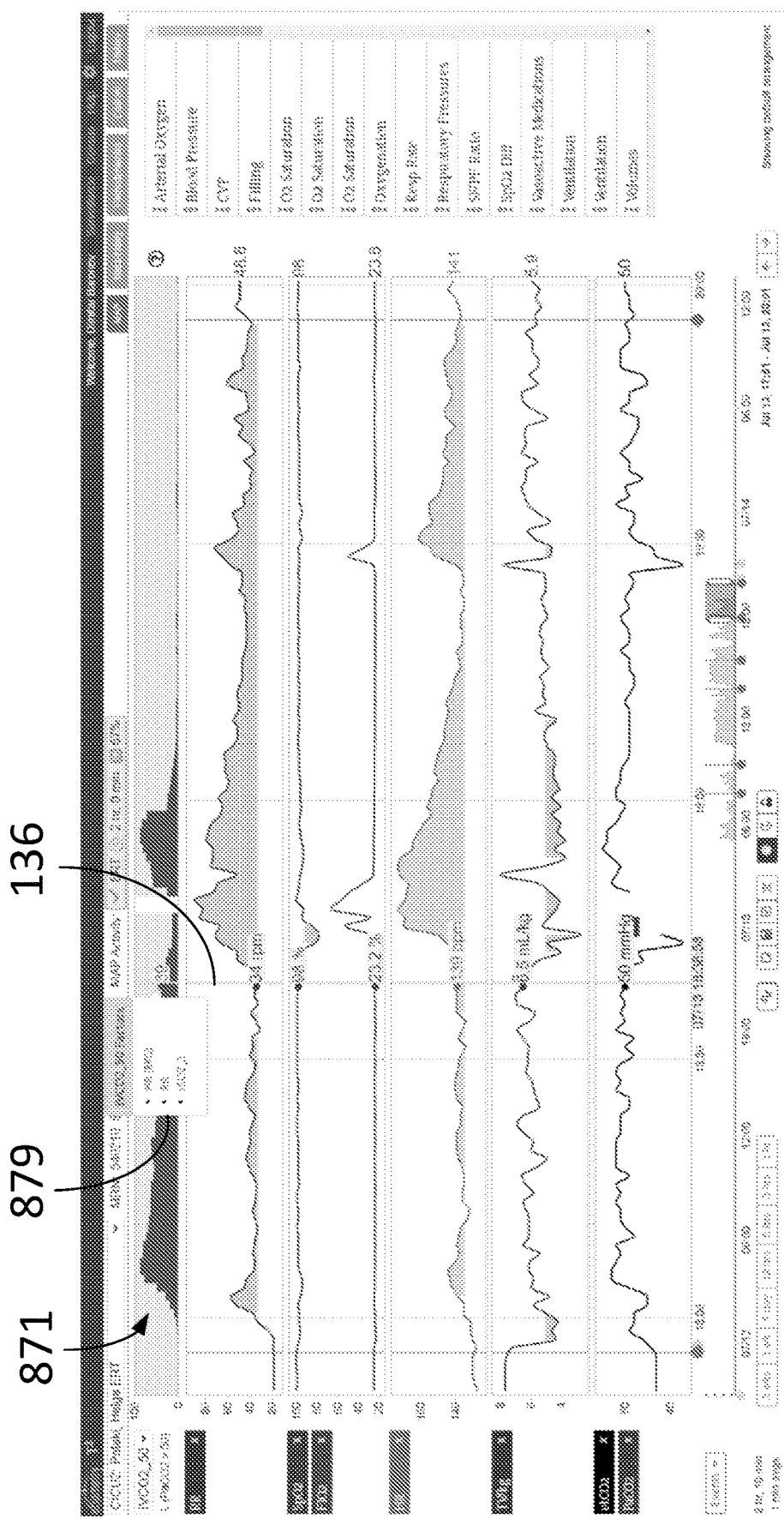

FIG. 13G schematically shows a time stamp of selected data for a particular moment of FIG. 13E. As indicated by the time-stamp line 136, the particular patient data values at a particular moment may be viewed. Furthermore, the influence of internal state variables on a patient's clinical risk is also visualized. For example, FIG. 13G shows the impact on a patient's clinical risk of low IVCO2 based on measured heart rate, respiratory rate, and rSO2.

In this example, while the IVCO2 index is not part of the particular protocol, it is provided for added context. This is a feature of the system where not all of the trends that are associated with a particular protocol view are rules. Some of them are displayed to provide context and facilitate the interpretation of why the rules are violated.

Although IVCO2 is shown as an example of a hidden state variable, the principles apply to any display of clinical risk and its associated internal state variable. As shown, FIG. 3D depicts one embodiment of the display of the influence of an internal state variable or measurement of an internal state variable on a patient's clinical risk. The user interface 112 shows the clinical risk plotted as a bar graph vs time at the top of the figure, as well as the monitored measurements for the patient plotted vs time below the risk bar graph. When the user hovers over the clinical risk graph 871, the measurements or ISVs that are contributing to the clinical risk level at that time are displayed in a box 879. The box 879 in the figure displays a non-limiting example of the top three contributing factors listed in order based on the amount of influence each contributor has had on the displayed risk level. By scrolling alone the time-axis, the top 3 contributing factors may change from time to time. Furthermore, some embodiments may display more than 3 or fewer than 3 contributing factors.

FIGS. 13A-13G provide a user interface 112 that may be displayed in a number of ways. For example, the interface 112 may be provided on any conventional interface (e.g., a monitor, touch-screen display, etc.). Additionally, the interface 112 may be stored on a server that can be co-located in the hospital network, or that can be remotely access (e.g., from the cloud). In some embodiments, a dedicated device may display the user interface 112. The device may have a touch-screen display, wireless internet connectivity, and/or may be configured to mount to a hospital bed.

It should be understood that illustrative embodiments advantageously enable a number of improved medical care applications, and furthermore provide improved medical outcomes that would otherwise not be possible without the real-time tracking of patient parameters. The state-of-the-art checks patient parameters statically, (e.g., on a particular patient schedule or based on a medical practitioner schedule). However, the inventors determined that patient clinical outcomes are far improved when eligibility time is reduced, and/or when dynamic concordance rate is maintained at a high level. By having real-time visualization of the eligibility time and/or the dynamic concordance rate, patients may more quickly enter an eligible protocol, and may also be treated more quickly to help keep dynamic concordance rate high. Furthermore, the specific issues with dynamic concordance rate may be visualized in real-time and specific low compliance parameters may be easily determined by medical practitioners.

There are a large number of protocols which may be implemented by illustrative embodiments of the invention. Non-limiting examples of protocols include:

Ventilation of patients with Acute Respiratory Distress Syndrome. Eligibility criteria may be defined by SF (SpO2/FIO2) or PF (PaO2/FIO2) ratio being below 300. Compliance may be defined by specific parameters indicting appropriate ventilator settings, e.g:
Tidal Volume below 8 ml/kg
peak respiratory pressure below 30 cmH2O Weaning of Vasoactive Support. Eligibility criteria may be defined by a low risk for the patient being in an inadequate oxygen delivery state as assessed by the system and method in U.S. patent application Ser. No. 17/033,591, which is incorporated herein by reference in its entirety. After initiating of weaning of Vasoactive Support compliance may be defined as:
Rate of VIS score decrease for each consecutive hour being above a given threshold
Risk for inadequate oxygen delivery not being above a given threshold
Mean arterial blood pressure not decreasing below a patient and age specific threshold
Lactate not increasing above 4 mmol/L As referenced previously, various protocols 120 may include eligibility rules 122 and/or compliance rules 124 may include conditions (e.g., true or false, a certain variable is greater than a particular value, etc.) that reference hidden state variables. Details of calculating risk probabilities for certain patient conditions are described in further detail in co-pending U.S. patent application No. 63/091,427, which is incorporated herein by reference in its entirety.

Various embodiments of the invention may be implemented at least in part in any conventional computer programming language. For example, some embodiments may be implemented in a procedural programming language (e.g., "C"), as a visual programming process, or in an object oriented programming language (e.g., "C++"). Other embodiments of the invention may be implemented as a pre-configured, stand-along hardware element and/or as preprogrammed hardware elements (e.g., application specific integrated circuits, FPGAs, and digital signal processors), or other related components.

In an alternative embodiment, the disclosed apparatus and methods (e.g., see the methods described above) may be implemented as a computer program product for use with a computer system. Such implementation may include a series of computer instructions fixed either on a tangible, non-transitory, non-transient medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware (e.g., a processor). Still other embodiments of the invention are implemented as entirely hardware, or entirely software.

Although the above discussion discloses various exemplary embodiments of the invention, it should be apparent that those skilled in the art can make various modifications that will achieve some of the advantages of the invention without departing from the true scope of the invention.

What is claimed is:

1. A computer-implemented system for determining patient eligibility and compliance with a medical protocol, the system comprising:
    a medical protocol library containing information relating to a plurality of medical protocols including at least one parent protocol and at least one child protocol, the information including:
        an eligibility rule for the parent protocol, a compliance rule for the parent protocol, an eligibility rule for the child protocol, and a compliance rule for the child protocol,
    each of the eligibility rules having at least one condition, and each of the compliance roles having at least one condition, wherein one or more conditions of the eligibility rule of the child protocol are dependent upon the parent protocol;
    a sensor and medical device interface configured to receive patient data from one or more sensors and/or one or more medical devices;
    a protocol eligibility module configured to alert a medical practitioner to initiate the parent protocol for the patient; and
    a protocol compliance module configured to determine, after the patient begins the parent protocol, a dynamic concordance rate of the at least one patient for the parent protocol as a function of the received patient data and the compliance rule of the parent protocol, wherein the dynamic concordance rate defines the rate at which the patient data is consistent with the compliance rule of the parent protocol over a period of time,
    wherein the protocol eligibility module is further configured to determine patient eligibility for a child protocol as a function of the dynamic concordance rate of the at least one parent protocol,
    the user interface being further configured to alert a medical practitioner that the patient is eligible for the child protocol as a function of the dynamic concordance rate of the parent protocol for the patient.

2. The system as defined by claim 1, further comprising a quality reporting module configured to determine an eligibility time, wherein the eligibility time is the amount of time elapsed from when the at least one patient becomes eligible for the parent protocol or the child protocol to the time the at least one patient is entered into the parent protocol or the child protocol, wherein the user interface is further configured to display the eligibility time for the at least one patient.

3. The system as defined by claim 1, wherein the protocol eligibility module is configured to determine patient eligibility as a function of a hidden state variable.

4. The system as defined by claim 1, wherein at least one condition of the eligibility rules for the child protocol include a parametric condition.

5. The system as defined by claim 1, wherein the protocol eligibility module is configured to determine patient eligibility as a function of a patient electronic medical record.

6. The system as defined by claim 1, wherein the user interface is configured to display, in response to a user selection of a selected patient, all of the received patient data relating to the eligibility rule and/or the compliance rules of a corresponding protocol that the selected patient is on.

7. The system as defined by claim 6, wherein non-compliant portions of the received data are visually distinguishable from compliant portions of the data.

8. The system as defined by claim 1, wherein the patient eligibility is determined as a function of meeting a plurality of conditions and/or patient variables.

9. The system as defined by claim 1, wherein the medical protocol is an extubation readiness trial protocol.

10. A computer-implemented method for entering a patient in a medical protocol, the method comprising:
    receiving an eligibility rule and a compliance rules for a parent protocol;
    receiving real-time patient data from one or more sensors and/or medical devices, wherein the patient data directly or indirectly relates to the eligibility rule for the parent protocol;
    determining that the patient is eligible for the parent protocol as a function of the eligibility rule of the parent protocol and the real-time patient data from the one or more sensor and/or medical devices;
    alerting a medical practitioner that the patient is eligible for the parent protocol;
    receiving real-time patient data from one or more sensors and/or medical devices, wherein the patient data directly or indirectly relates to the compliance rules for the parent protocol;
    calculating a dynamic concordance rate for the parent protocol, the dynamic concordance rate for the parent protocol indicating the rate at which the patient data is consistent with the compliance rule for the parent protocol over a period of time;
    receiving an eligibility rule for a child protocol, wherein at least one condition of the eligibility rule of the child protocol is dependent at least upon the dynamic concordance rate of the parent protocol;

receiving real-time patient data from one or more sensors and/or medical devices, wherein the patient data directly or indirectly relates to the eligibility rule for the child protocol;

alerting a medical practitioner that the patient is eligible for the child protocol.

11. The method as defined by claim 10, further comprising:

entering the patient into the medical protocol after indicating that the patient is eligible for the protocol.

12. The method as defined by claim 11, further comprising:

displaying, on a user interface, a plurality of patients that are eligible for the protocol and/or currently enrolled in the protocol;

tracking a time since the patient became eligible for the protocol and/or a time since the patient is enrolled in the protocol;

tracking a dynamic concordance rate of the medical protocol;

displaying, on the user interface, the time since the patient became eligible for the protocol, the time since the patient is enrolled in the protocol, and the dynamic concordance rate of the medical protocol.

13. The method as defined by claim 12, further comprising:

displaying, in response to a user selection of a given protocol, the received patient data that relates to the eligibility rule and/or the compliance rule for the selected protocol.

14. The method as defined by claim 13, wherein the received patient data is used to determine a hidden state variable.

15. The method as defined by claim 14, wherein the eligibility rules and/or the compliance rules for the selected protocol include a hidden state variable risk.

16. The method as defined by claim 11, wherein determining patient eligibility is a function of a patient electronic medical record.

17. The method as defined by claim 10, further comprising displaying the indication that the patient is eligible for the protocol.

18. The method as defined by claim 11, wherein the medical protocol is an extubation readiness trial protocol.

19. A computer program product for use on a computer system for determining eligibility and compliance with a medical protocol, the computer program product comprising a tangible, non-transient computer usable medium having computer readable program code thereon, the computer readable program code comprising:

program code configured to receive an eligibility rule and a compliance rule for a parent protocol;

program code configured to receive real-time patient data from one or more sensors and/or medical devices, wherein the patient data directly or indirectly relates to the eligibility rule for the parent protocol;

program code configured to determine that the patient is eligible for the parent protocol as a function of the eligibility rule of the parent protocol and the real-time patient data from the one or more sensor and/or medical devices;

program code configured to alert a medical practitioner that the patient is eligible for the parent protocol;

program code configured to receive real-time patient data from one or more sensors and/or medical devices, wherein the patient data directly or indirectly relates to the compliance rule for the parent protocol;

program code configured to calculate a dynamic concordance rate for the parent protocol, the dynamic concordance rate for the parent protocol indicating the rate at which the patient data is consistent with the compliance rules for the parent protocol over a period of time;

program code configured to receive an eligibility rule for a child protocol, wherein at least one condition of the eligibility rules of the child protocol is dependent upon the dynamic concordance rate of the parent protocol;

program code configured to receive real-time patient data from one or more sensors and/or medical devices, wherein the patient data directly or indirectly relates to the eligibility rules for the child protocol;

program code configuring to alert a medical practitioner that the patient is eligible for the child protocol.

20. A computer program product as defined by claim 19, further comprising:

program code configured to display, on a user interface, a plurality of patients that are eligible for the protocol and/or currently enrolled in the protocol;

program code configured to track a time since the patient became eligible for the protocol and/or a time since the patient is enrolled in the protocol;

program code configured to track a dynamic concordance rate of the medical protocol;

program code configured to display, on the user interface, the time since the patient became eligible for the protocol, time since the patient is enrolled in the protocol, and the dynamic concordance rate of the medical protocol.

\* \* \* \* \*